United States Patent [19]
Christ et al.

[11] Patent Number: 5,935,938
[45] Date of Patent: *Aug. 10, 1999

[54] SUBSTITUTED LIPOSACCHARIDES USEFUL IN THE TREATMENT AND PREVENTION OF ENDOTOXEMIA

[75] Inventors: William J. Christ; Daniel P. Rossignol, both of Andover, Mass.; Seiichi Kobayashi, Ibarakiken; Tsutomu Kawata, Ibaraki, both of Japan

[73] Assignee: Eisai Co., Ltd., Bunkyo-ku, Japan

[ * ] Notice: This patent is subject to a terminal disclaimer.

[21] Appl. No.: 08/658,656

[22] Filed: Jun. 5, 1996

Related U.S. Application Data

[63] Continuation-in-part of application No. 08/461,675, Jun. 5, 1995, Pat. No. 5,750,664.

[51] Int. Cl.$^6$ .............................. A61K 31/70; C13K 5/00
[52] U.S. Cl. ..................... 514/53; 536/17.2; 536/17.9; 536/123.13
[58] Field of Search ................... 536/4.1, 17.2, 536/17.9, 123.13; 514/25, 53

[56] References Cited

U.S. PATENT DOCUMENTS

| | | |
|---|---|---|
| 4,495,346 | 1/1985 | Anderson et al. . |
| 4,987,237 | 1/1991 | Myers et al. ............................ 549/222 |
| 5,066,794 | 11/1991 | Shiba . |
| 5,530,113 | 6/1996 | Christ et al. ....................... 536/123.13 |

FOREIGN PATENT DOCUMENTS

| | | |
|---|---|---|
| 0 172 581 A2 | 2/1986 | European Pat. Off. . |
| 3-135990 | 6/1991 | Japan . |
| 2 179 945 | 3/1987 | United Kingdom . |
| 2 220 211 | 1/1990 | United Kingdom . |
| WO 91/01134 | 2/1991 | WIPO . |

OTHER PUBLICATIONS

Bone et al., "Definitions for Sepsis and Organ Failure and Guidelines for the Use of Innovative Therapies in Sepsis", *Chest: The Cardiopulmonary J.*, 101:1644–55 (1992).

Knaus et al., "The Apache III Prognostic System: Risk Prediction of Hospital Mortality for Critically Ill Hospitalized Adults", *Chest: The Cardiopulmonary J.*, 100:1619–36 (1991).

Knaus et al., "Recommendations for Use of Folic Acid to Reduce Number of Spina Bifida Cases and Other Neural Tube Defects", *JAMA*, 269:1233–41 (1993).

Rose et al., "Agonistic and Antagonistic Activities of Bacterially Derived Rhodobacter Sphaeroides Lipid A: Comparison with Activities of Synthetic Material of the Proposed Structure and Analogs", *Infection and Immunity*, 63:833–39 (1995).

Ruff et al., "Tumor Necrosis Factor", *Lymphokines: A Forum for Immunoregulatory Cell Products; Academic Press* 2:235–72 (1981).

Schwartz et al., "Endotoxin Responsiveness and Grain Dust– induced Inflammation in the Lower Respiratory Tract", *Am. J. Physiol.*, 267:1609–17 (1994).

Vogel et al., "BCG–Induced Enhancement of Endotoxin Sensitivity in C3H/HeJ Mice", *J. Immunology*, 124:2004–2009 (1980).

Takayama et al., Infection and Immunity 57:1336–1338, 1989.

*Primary Examiner*—Elli Peselev
*Attorney, Agent, or Firm*—Clark & Elbing, LLP

[57] ABSTRACT

Novel substituted liposaccharides useful as in the prophylactic and affirmative treatment of endotoxemia including sepsis, septicemia and various forms of septic shock and methods of using these agents are provided. Also provided are methods of preparing these agents and intermediates useful therein.

13 Claims, 3 Drawing Sheets

Compound 1 Inhibits LPS-induced TNF in Human Whole Blood

SUBSTITUTED LIPOSACCHARIDES USEFUL IN THE TREATMENT AND PREVENTION OF ENDOTOXEMIA

RELATED APPLICATIONS

This application is a continuation-in-part of Ser. No. 08/461,675, filed Jun. 5, 1995 now U.S. Pat. No. 5,750,664.

FIELD OF INVENTION

This invention relates to compounds which are useful as in the prophylactic and affirmative treatment of endotoxin exposure including sepsis, septicemia, endotoxemia and various forms of septic shock.

BACKGROUND OF THE INVENTION

The invention relates to analogs of Lipid A which are useful as inhibitors of endotoxemia.

The incidence of gram negative bacteremia in the United States has been estimated to be approximately 100,000 to 300,000 cases per year, with a mortality rate of 30–60%. Antibiotics are commonly used as the primary chemotherapy for this disease; however, their bactericidal action can result in disruption of the bacterium and concomitant release of endotoxin, i.e., the lipopolysaccharide (LPS) moiety of the bacterial outer membrane. The liberated LPS induces a number of pathophysiological events in mammals (collectively referred to as gram-negative endotoxemia or sepsis syndrome). These include fever, generalized inflammation, disseminated intravascular coagulation (DIC), hypotension, acute renal failure, acute respiratory distress syndrome (ARDS), hepatocellular destruction and cardiac failure.

Although endotoxin initiates septic shock, it has little or no direct toxic effect on tissues; instead, it triggers an immunobiological response leading to a cascade of release of cytokines such as tumor-necrosis factor (TNF), interleukin-1, interleukin-6 and interleukin-8, and other biological mediators such as nitric oxide, as well as an array of secondary mediators (e.g., prostaglandins, leukotrienes, interferons, platelet-activating factor, endorphins and colony-stimulating factors). Generation of pathophysiological concentrations of these cytokines and inflammatory mediators influence vasomotor tone, microvascular permeability and the aggregation of leukocytes and platelets causing a syndrome termed systemic inflammatory response syndrome (or SIRS) and septic shock.

The bacterial lipopolysaccharide molecule has three main regions: a long chain polysaccharide (O Antigen), a core region and a Lipid A region. The entire lipopolysaccharide molecule, as well as some of its individual components possess toxic effects described above. Most of these toxic effects, however, are believed to be attributable to the Lipid A portion. Structurally, Lipid A is composed of a diphosphorylated disaccharide acylated by long chain fatty acids.

Therapies for endotoxin-related diseases have generally been directed towards controlling the inflammatory response. Such therapies include corticosteriod treatment, suggested to ameliorate endotoxin-mediated cell membrane injury and to reduce production of certain biological mediators; administration of antibodies designed to neutralize bacterial LPS; treatment with agents to suppress hypotension or with naloxone which apparently blocks the hypotensive effects associated with sepsis syndrome; and treatment with nonsteroidal anti-inflammatory drugs, purported to block cyclooxygenanses and thereby decrease the production of certain secondary mediators such as prostaglandins and thromboxane.

However, none of these therapies to date has resulted in significant reduction in the morbidity and mortality resulting from sepsis and septic shock syndrome. Thus there is a long felt need for agents to affirmatively treat this disorder.

Christ, et al., "Anti-Endotoxin Compounds," U.S. Ser. No. 07/935,050, filed Aug. 25, 1992, the contents of which are included by reference, disclose certain disaccharide compounds, such as B531 shown below, useful for the treatment of endotoxemia.

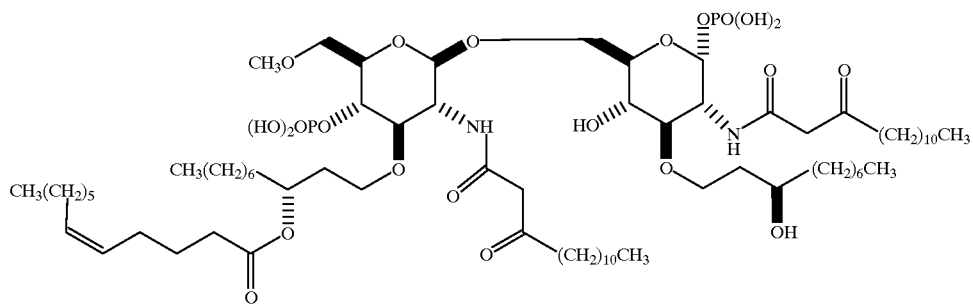

B531

Other references which disclose certain lipodisaccharides include Macher, et al., Great Britain patent 2,179,945, Meyers, et al., Great Britain patent 2,220,211, Shiba, et al., European patent 172,581, Anderson, et al., U.S. Pat. No. 4,495,346 and Shiba, et al., U.S. Pat. No. 5,066,794.

SUMMARY OF THE INVENTION

The present invention is directed to the treatment of sepsis, septic shock, endotoxemia and related disorders using novel liposaccharide analogs. The compounds of the present invention possess advantages for pharmaceutical use such as enhanced pharmacological selectivity, efficacy, and in particular increased persistence of action. A representative compound of this invention, compound 1, is shown below:

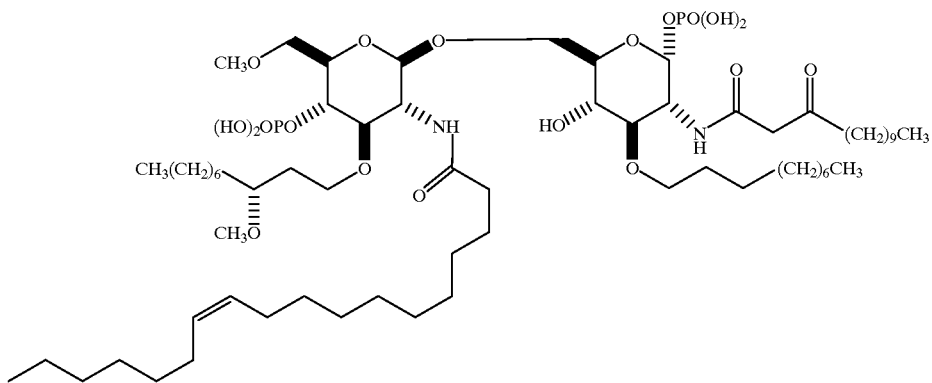

Compound 1

Further, the present invention is directed to the prophylactic and affirmative treatment of any LPS-mediated disorder. These disorders include, but are not limited to, sepsis, septicemia (including but not limited to endotoxemia), endotoxemia resulting from gram negative bacteremia (with its accompanying symptoms of fever, generalized inflammation, disseminated intravascular coagulation, hypotension, acute renal failure, acute respiratory distress syndrome, adult respiratory distress syndrome (ARDS), hepatocellular destruction and/or cardiac failure) and various forms of septic shock (including but not limited to endotoxic shock). Also, compounds of this invention will be useful in the prophylactic or affirmative treatment of localized or systemic inflammatory response to infection by different types of organisms, including gram negative bacteria, and in diseases related to translocation of gram negative bacteria or endotoxin from the gut.

Together these disorders are termed systemic inflammatory response syndrome or SIRS (For a discussion of these terms, see Bone, et al., Chest 1992; 101: 1644–55).

Definitions

In accordance with the present invention and as used herein, the following terms, are defined with the following meanings, unless explicitly stated otherwise.

The term "alkyl" refers to aliphatic organic groups which may be branched or straight and which may be optionally substituted with one or more halogen atoms at any position along the alkyl chain. Alkyl groups include both groups which are have a single unoccupied valence, for example, —$CH_2$—$CH_3$ and alkylene groups which have two unoccupied valences, for example —$CH_2$—$CH_2$—. As is obvious to those skilled in the art, the single or double unoccupied valence will be used as appropriate to describe compounds which are chemically stable.

The term "prodrug" as used herein refers to any compound that has less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, phosphates and urethanes, included herein as examples. The groups illustrated are exemplary, not exhaustive and one skilled in the art could prepare other known varieties of prodrugs. Such prodrugs of the compounds of Formula I fall within the scope of the present invention.

The term "pharmaceutically acceptable salt" includes salts of compounds of Formula I derived from the combination of a compound of this invention and an organic or inorganic acid or base. The compounds of Formula I are useful in both non-ionized and salt form. In practice the use of salt form amounts to use of base form; both forms are within the scope of the invention.

The term "geometric isomers" refers to "trans" or "cis" (or "entgegen" or "zusammen") isomers as generally understood by those skilled in the art. All geometric isomers are within the scope of the invention.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer. It is evident that in addition to the sugar moiety, additional asymmetric carbons may be present in compounds of Formula I, for example being present in the side chains. In this event, all of the resulting diastereomers are considered to fall within the scope of the present invention.

DETAILED DESCRIPTION OF THE INVENTION

Novel Liposaccharides

Figure 1:
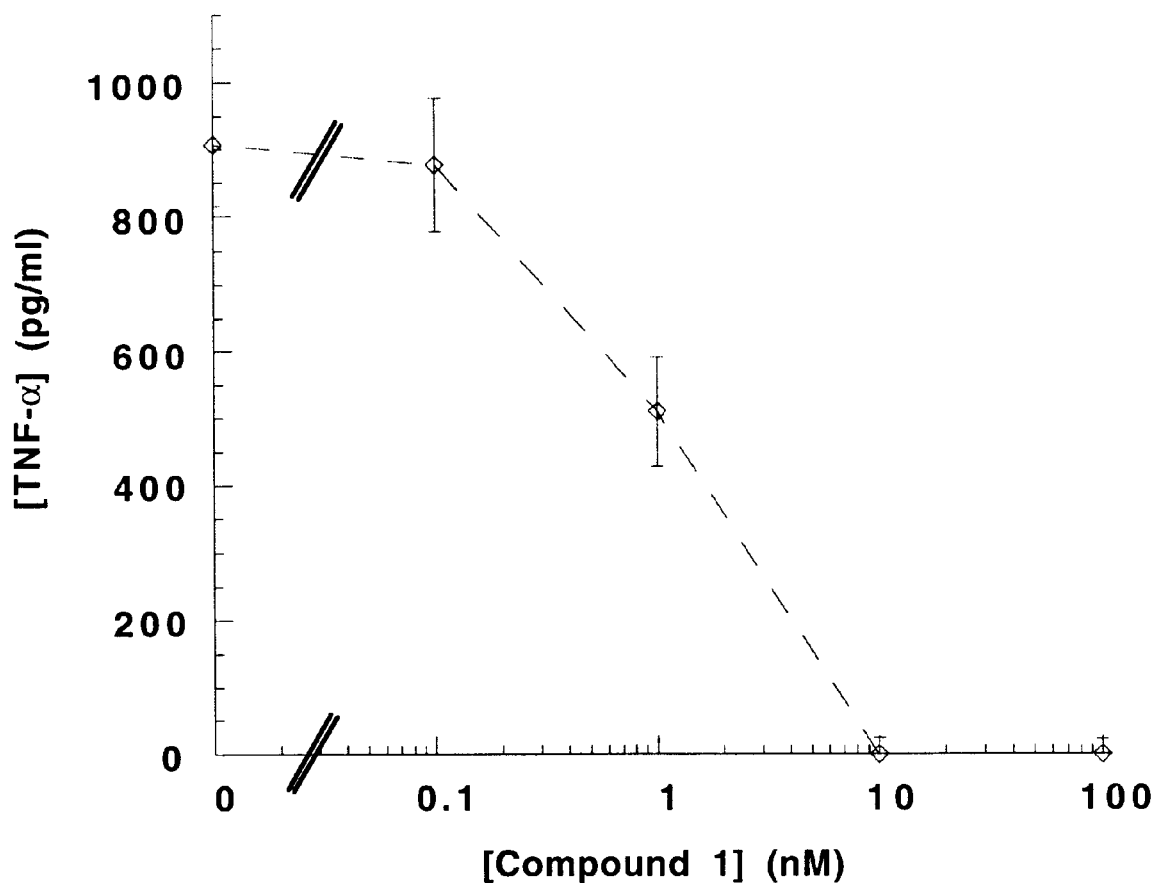
FIG. 1 depicts the inhibition of release of TNF-α by Compound 1 illustrating the inhibition of LPS-mediated induction of tumor necrosis factor (TNF) in human whole blood by a compound of this invention.

In one aspect, the present invention relates to the novel use of substituted liposaccharides which comprise compounds of the general formula I.

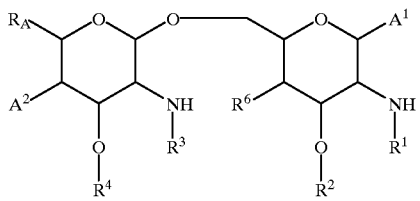

where $R^1$ is selected from the group consisting of

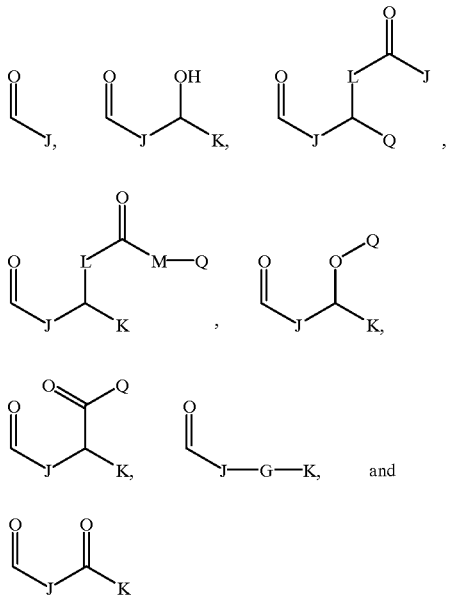

where each J, K and Q, independently, is straight or branched C1 to C15 alkyl; L is O, NH, or $CH_2$; M is O or NH; and G is NH, O, S, SO, or $SO_2$;

$R^2$ is straight or branched C5 to C18 acyl;

$R^3$ is selected from the group consisting of straight or branched C5 to C15 alkyl,

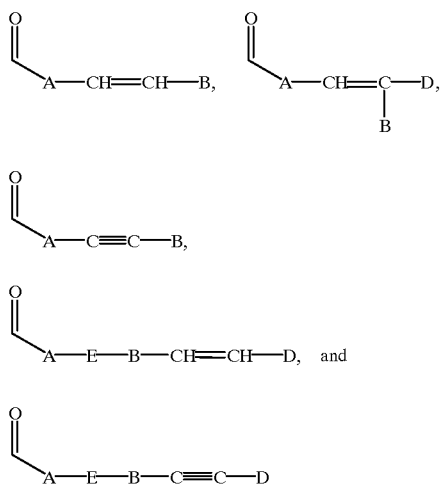

where E is NH, O, S, SO, or $SO_2$; each A, B and D, independently, is straight or branched C1 to C15 alkyl;

$R^4$ is selected from the group consisting of straight or branched C4 to C20 alkyl, and

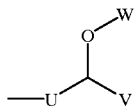

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J',—J'—OH,—J'—O—K',—J'—O—K'—OH, and —J'—O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of

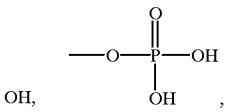

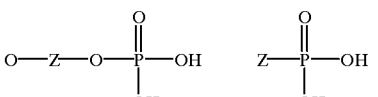

where Z is straight or branched C1 to C10 alkyl;

and pharmaceutically acceptable salts thereof.

Embodiments of the above formula include the following or combinations of the following:

$R^2$ is C8 to C15 straight or branched alkyl;

$R^2$ is C9 to C12 straight or branched alkyl;

$R^2$ is C10 straight or branched alkyl;

$A^1$ and $A^2$, independently, are OH or —O—PO(OH)$_2$;

$R^6$ is hydroxy;

$R^5$ is C1 to C5 straight or branched alkyl;

$R^1$ is selected from the group consisting of

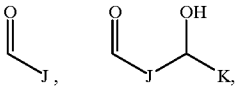

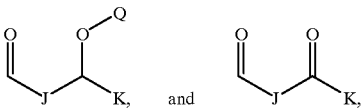

where each J, K and Q, independently, is straight or branched C1 to C15 alkyl;

$R^3$ is selected from the group consisting of

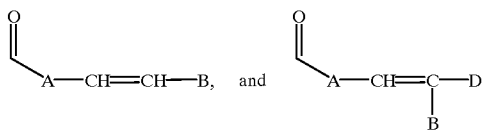

where each A, B and D, independently, is straight or branched C1 to C15 alkyl;
the double bonds of $R^3$ are cis or zusammen;
the double bonds of $R^3$ are trans or entgegen;
$R^4$ is selected from the group consisting of straight or branched C4 to C20 alkyl, and

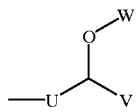

where U is straight or branched C2 to C5 alkyl, V is straight or branched C5 to C12 alkyl, and W is hydrogen or straight or branched C1 to C5 alkyl;
$R_A$ is $R^5$; and $R_A$ is $R^5$—O—CH2—.

In other embodiments, each $A^1$ and $A^2$, independently, is selected from the group consisting of OH and —O—PO(OH)$_2$;
$R^1$ is selected from the group consisting of

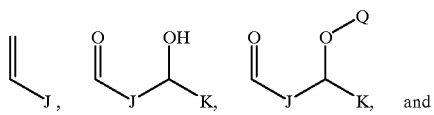

where each J, K and Q, independently, is straight or branched C1 to C15 alkyl;
$R^2$ is straight or branched C8 to C15 alkyl;
$R^3$ is selected from the group consisting of

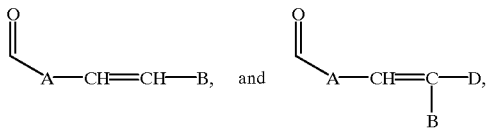

where each A, B and D, independently, is straight or branched C1 to C15 alkyl;
$R^4$ is

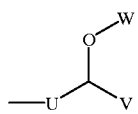

where U is straight or branched C2 to C5 alkyl, V is straight or branched C5 to C12 alkyl and W is hydrogen or straight or branched C1 to C5 alkyl;

and $R^5$ is straight or branched C1 to C5 alkyl; and
$R^6$ is hydroxy.

In another embodiment, $A^1$ and $A^2$ are —O—PO(OH)$_2$;
$R^1$ is selected from the group consisting of

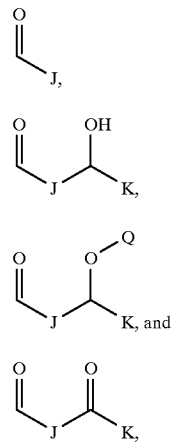

where each J and Q, independently, is straight or branched, C1 to C5 alkyl, and K is straight or branched C8 to C15 alkyl;
$R^2$ is straight or branched C8 to C15 alkyl;
$R^3$ is

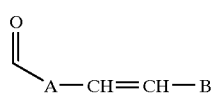

where A is straight or branched C5 to C12 alkyl and B is straight or branched C6 to C12 alkyl;
$R^4$ is

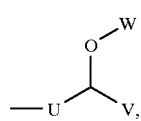

where U is straight or branched C2 to C5 alkyl, V is straight or branched C5 to C12 alkyl and W is hydrogen or straight or branched C1 to C5 alkyl; and
$R^5$ is straight or branched C1 to C5 alkyl; and
$R^6$ is hydroxy.

In another embodiment, $A^1$ and $A^2$ are —O—PO(OH)$_2$;
$R^1$ is selected from the group consisting of

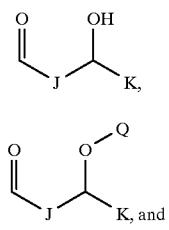

-continued

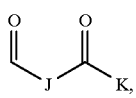

where each J and Q, independently, straight or branched is C1 to C3 alkyl, and K is straight or branched C10 to C12 alkyl;

$R^2$ is straight or branched C9 to C12 alkyl;

$R^3$ is

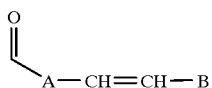

where A is straight or branched C8 to C12 alkyl and B is straight or branched C6 to C10 alkyl;

$R^4$ is

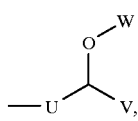

where U is straight or branched C2 to C4 alkyl, V is straight or branched C5 to C10 alkyl and W is hydrogen or straight or branched C1 to C3 alkyl; and $R^5$ is straight or branched C1 to C3 alkyl; and $R^6$ is hydroxy.

In another embodiment, $A^1$ and $A^2$ are —O—PO(OH)$_2$; $R^1$ is

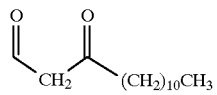

$R^2$ is (CH$_2$)$_9$CH$_3$;

$R^3$ is

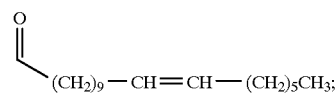

$R^4$ is

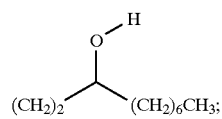

$R^5$ is —CH$_3$; and $R^6$ is hydroxy.

Also within the scope of the invention are compounds in which R1 and R3 are sulfonyls, i.e., compounds in which the carbonyl on these side chains is replaced with SO$_2$. These compounds could be prepared by treating the appropriately substituted alcoholic sugar with the appropriate alkylsulfonyl chloride. Thus R1 and R3 may also be selected from the following with A, B, D, E, J, K, L, Q. and M as defined above:

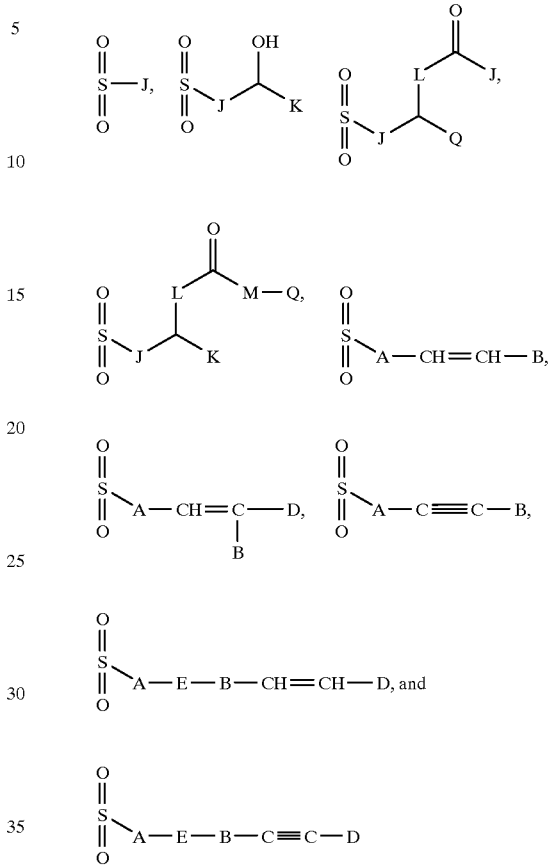

Further, within the scope of the invention are compounds in which the point of unsaturation within the R3 side chain is not a double or triple carbon-carbon bond but is an optionally substituted aromatic group, i.e., compounds in which R3 may have the following structure:

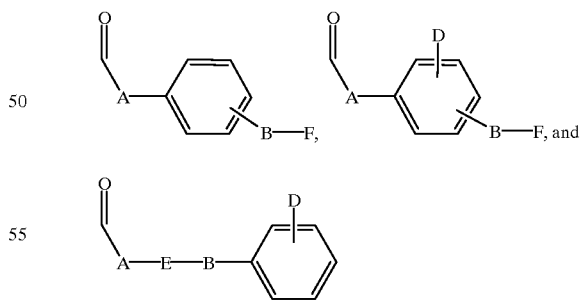

where E is NH, O, S, SO, or SO$_2$; each A is straight or branched C1 to C15 alkylene; D is straight or branched C1 to C15 alkyl; F is H, —OT, NT$^1$T$^2$, —CO2T, or phenyl wherein each of T, T$^1$, and T$^2$ is independently selected from hydrogen or C1 to C5 alkyl; B is straight or branched C1 to C15 alkyl;

In general, preferred are compounds where:

$R^1$ is selected from the group consisting of:

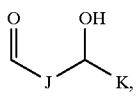
K,

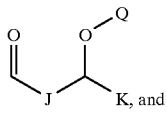
K, and

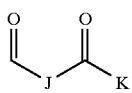
K where each J, K and Q independently, is straight or branched C1 to C15 alkyl;

$R^2$ is straight or branched C8 to C12 alkyl;

$R^3$ is selected from the group consisting of:

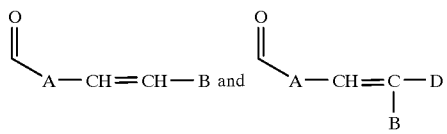

where each A, B and D, independently, is straight or branched C1 to C15 alkyl;

$R^4$ is

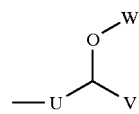

where U is straight or branched C2 to C5 alkyl, V is straight or branched C4 to C10 alkyl and W is hydrogen or straight or branched C1 to C5 alkyl;

$R^5$ is selected from the group consisting of: hydrogen, —J', and —J'OH where J' is C1 to C5 straight or branched alkyl;

$R^6$ is selected from the group consisting of hydroxy, halogen, and C1 to C5 acyloxy;

each $A^1$ and $A^2$, independently, are selected from the group consisting of: OH and

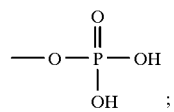

and pharmaceutically acceptable salts thereof.
Most preferred are compounds of formula 1 where:

$R^1$ is selected from the group consisting of:

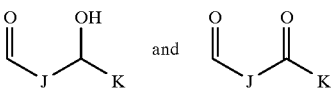

where J is straight or branched C1 to C5 alkyl and K is straight or branched C9 to C14 alkyl;

$R^2$ is straight or branched C8 to C12 alkyl;

$R^3$ is

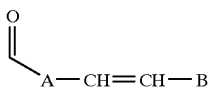

where A is straight or branched C6 to C12 alkyl and B is straight or branched C4 to C8 alkyl;

$R^4$ is

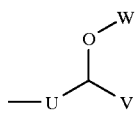

where U is straight or branched C2 to C4 alkyl, V is straight or branched C5 to C9 alkyl and W is hydrogen or straight or branched C1 to C3 alkyl;

$R^5$ is C1 to C3 straight or branched alkyl;

$R^6$ is hydroxy;

$A^1$ and $A^2$ are

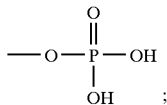

and pharmaceutically acceptable salts thereof.

General Synthetic Methods

This invention is also directed to processes for preparing compounds of Formula I. Disclosed herein are general synthetic routes for preparing variously substituted compounds of this invention. The synthesis for a compound of this invention, compound 1, is shown below.

Most of the reagents and starting materials are well known to those skilled in the art. Certain reagents and starting materials for this preparation are described in detail by Christ, et al., in U. S. application Ser. No. 07/935,050 which will issue as U.S. Pat. No. 5,530,113, the disclosure of which is hereby incorporated by reference.

One synthesis of the compounds of this invention is outlined below. Although this example describes the preparation of compound 1, use of alternate starting materials will yield other analogs of this invention. Thus the synthesis is indeed general in nature.

For example, use of alternative alkylating agents in synthetic step 22 will provide analogs with structurally differing substituents at R1.

The substitution pattern at R2 is controlled by the use of the proper alkylating agent in step 15.

Further, substitution of suitable alternative compounds in step 25 in the synthesis will produce analogs which differ with respect to R3.

Analogs without the oxygenated side chain at $R_A$ may be prepared by using slight variations in the synthetic scheme shown below as is will known to those skilled in the art. For the compound in which $R_A$ is methyl, for example, the product of synthetic step 8, the tosylate, could have this leaving group replaced by iodine in the Finklestein reaction. The iodo compound could be dehalogenated by treatment with zinc metal to give a methyl group at position $R_A$.

A representative synthesis of the R4 side chain is outlined below. The preparation of variations of this side chain may be achieved by replacing the starting material with other suitable starting materials. For example, the length or branching of this side chain may be prepared by starting with the appropriate starting material. Thus the use of alternative tosylates in step 6 will produce variation in R4.

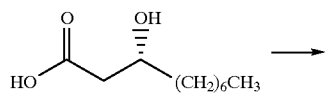

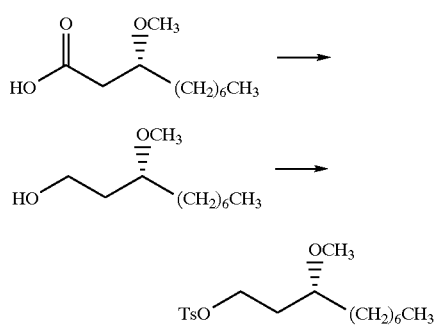

Thus the synthesis briefly outlined below provides versatile pathways to the compounds of this invention. (For details regarding the synthesis, see the following experimental examples.)

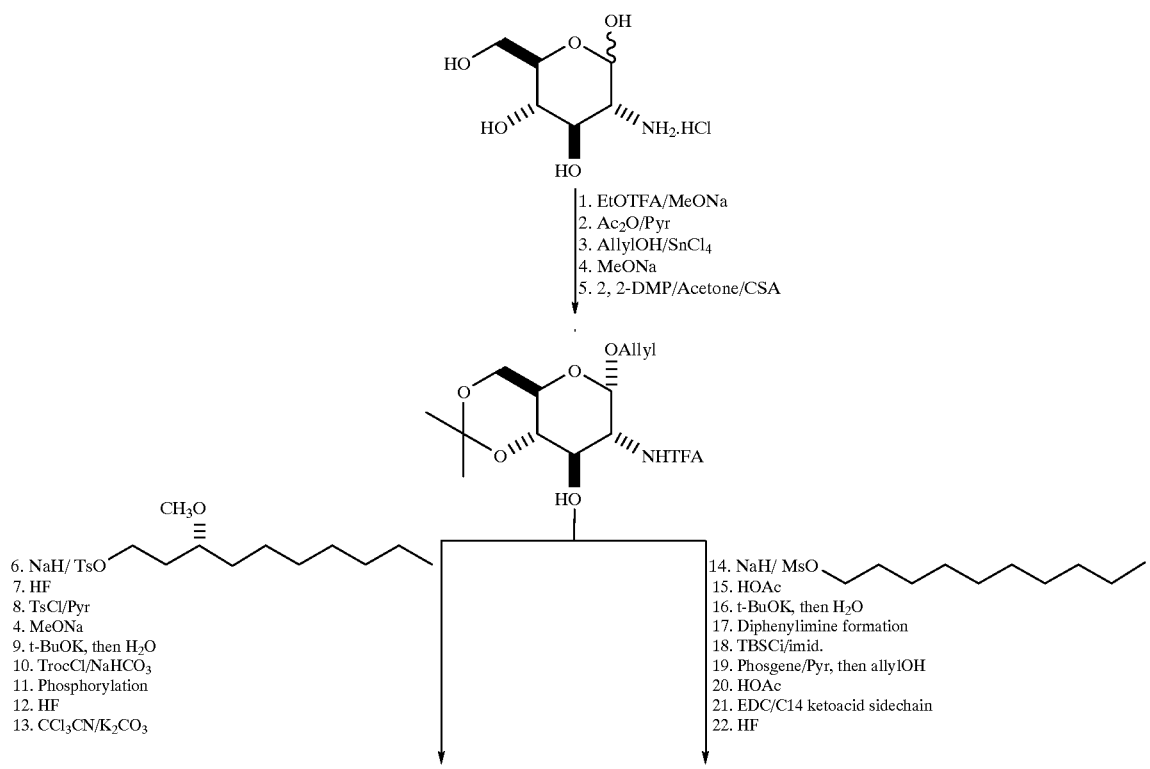

-continued

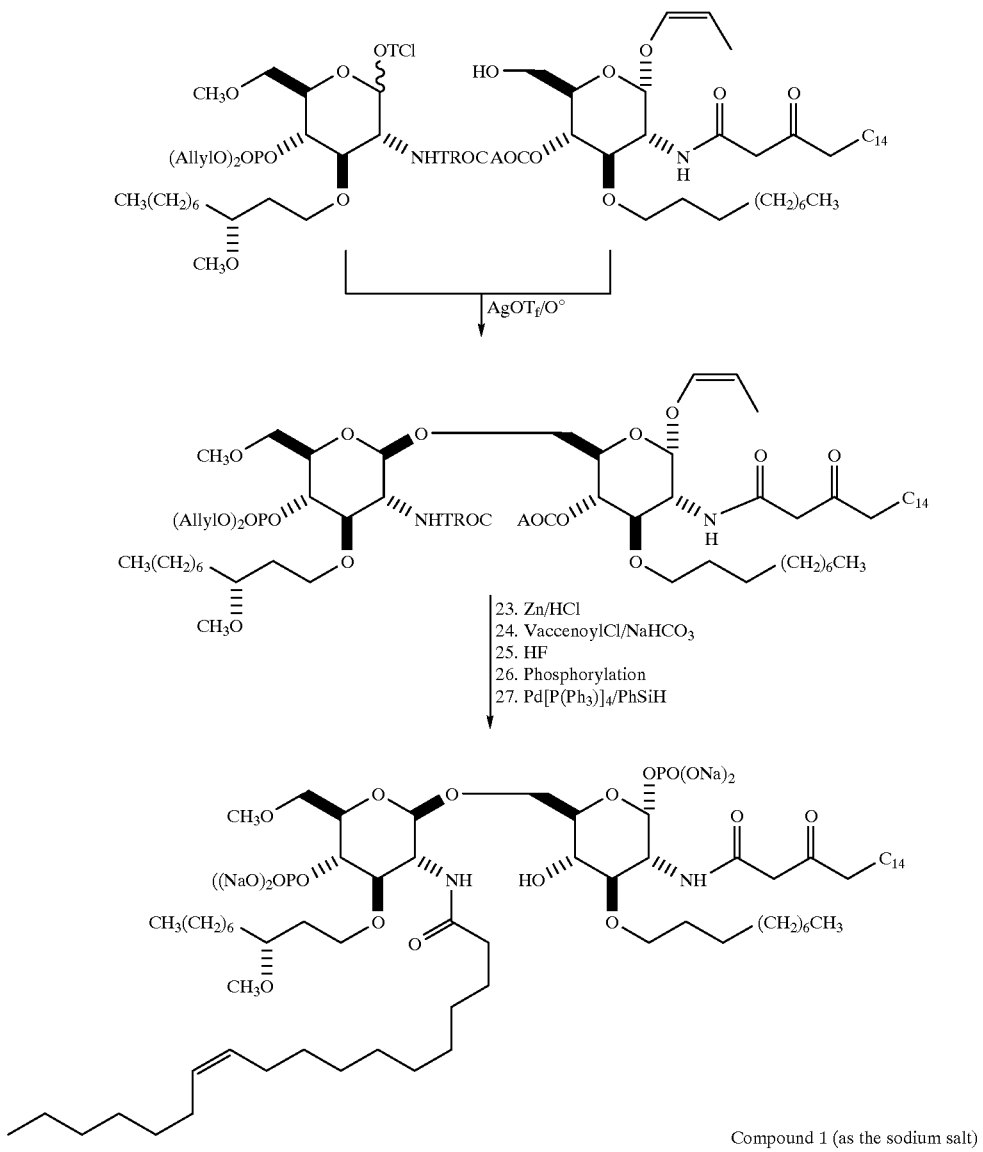

Compound 1 (as the sodium salt)

Applicants believe that the above route, Route 1, is the superior method of preparing compounds of the present invention due to a variety of factors such as use of cheaper starting materials, higher yields and the use of less toxic chemical agents, the route illustrated below, Route 2, may be used to prepare compounds of this invention.

Most of the reagents and starting materials are well known to those skilled in the art. Certain reagents and starting materials for this preparation are described in detail by Christ, et al., in U.S. application Ser. No. 07/935,050, the disclosure of which is hereby incorporated by reference. Although this example describes the preparation of compound 1, use of alternate starting materials will yield other analogs of this invention. Thus the synthesis is indeed general in nature.

For example, use of alternative alkylating agents in the preparation of intermediate U will provide analogs with structurally differing substituents at R1.

The substitution pattern at R2 is controlled by the use of the proper alkylating agent in the preparation of intermediate O.

Further, substitution of suitable alternative compounds for intermediate E in the preparation of intermediate G will produce analogs which differ with respect to R3.

A representative synthesis of the R4 side chain is outlined below. The preparation of variations of this side chain may be achieved by replacing the starting material with other suitable starting materials. For example, the length or branching of this side chain may be prepared by starting with the appropriate starting material. (For details regarding the synthesis, see the following experimental examples.)

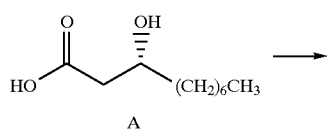

A

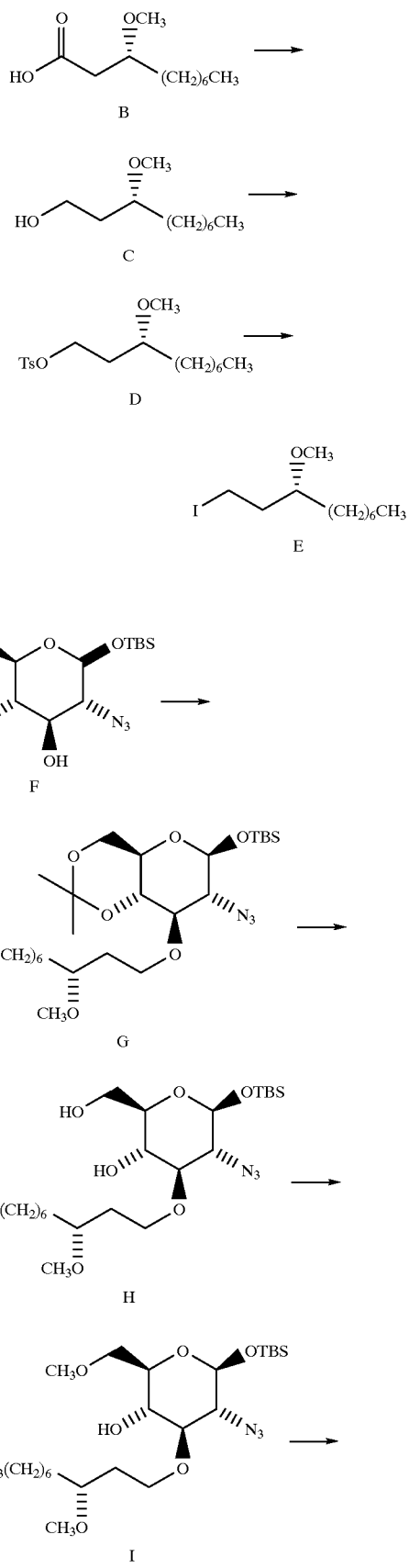
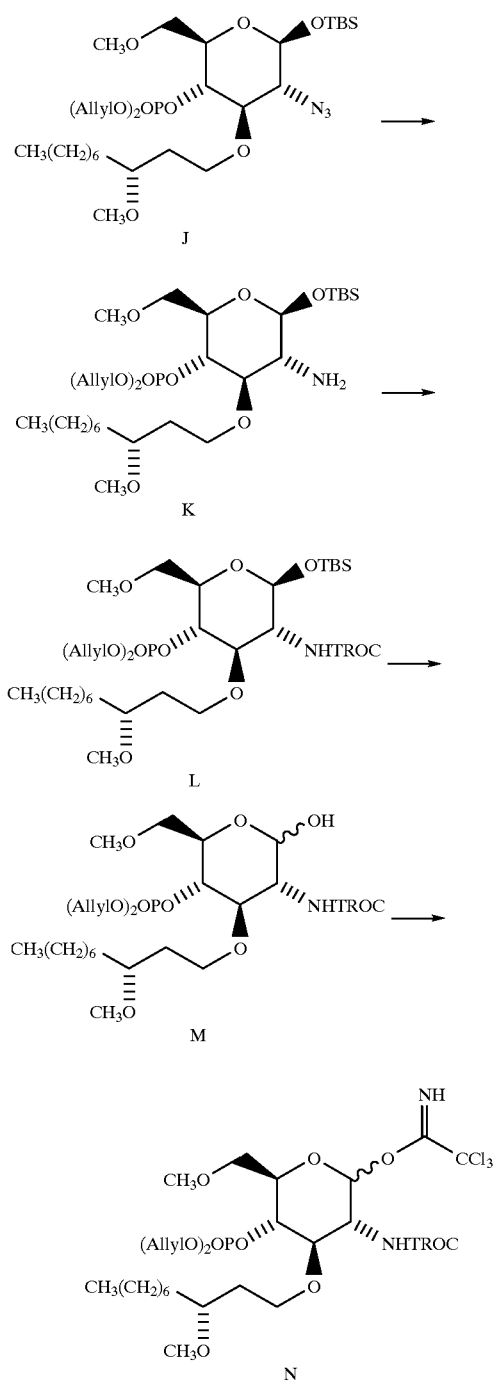
A representative preparation of the "left" portion is outlined below.
A representative synthesis of the "right" portion of compound 1 is shown below.

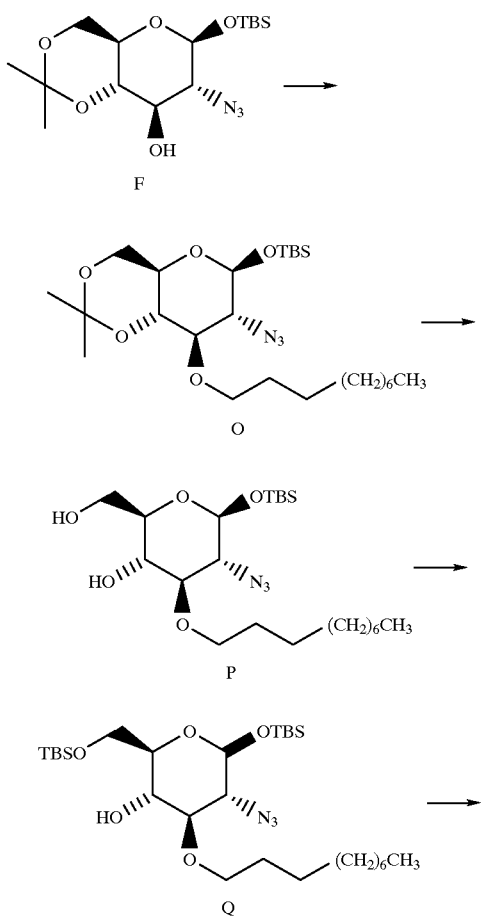
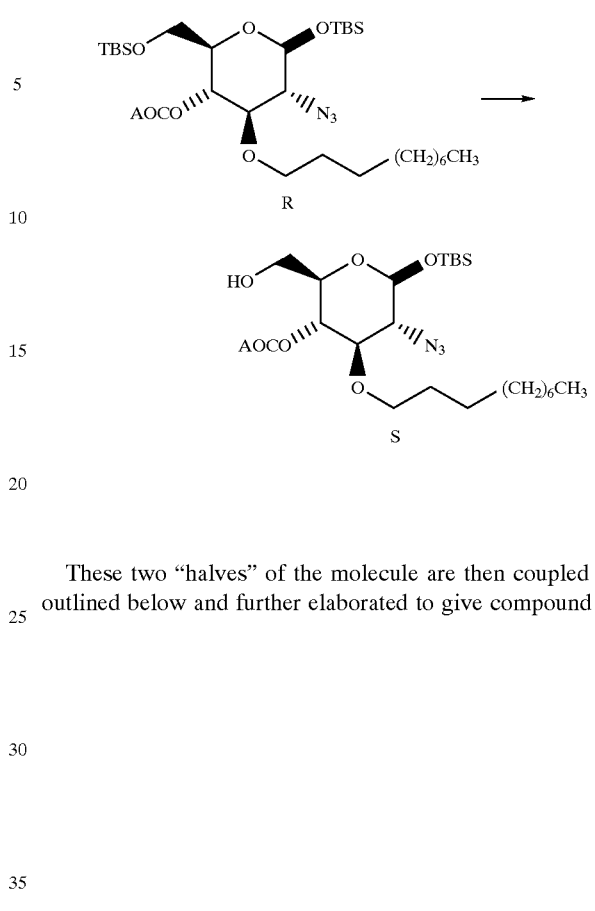
These two "halves" of the molecule are then coupled as outlined below and further elaborated to give compound 1.
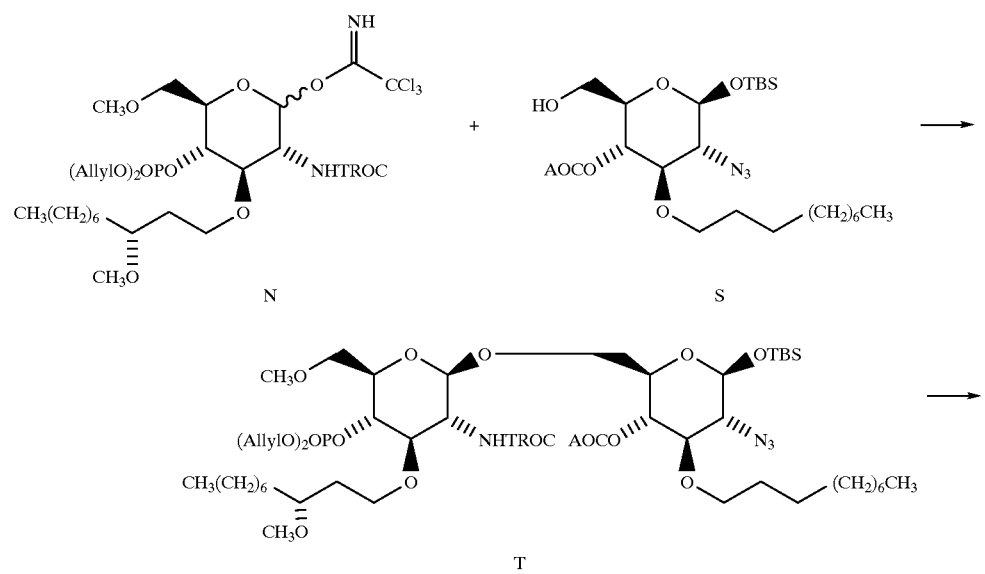

-continued
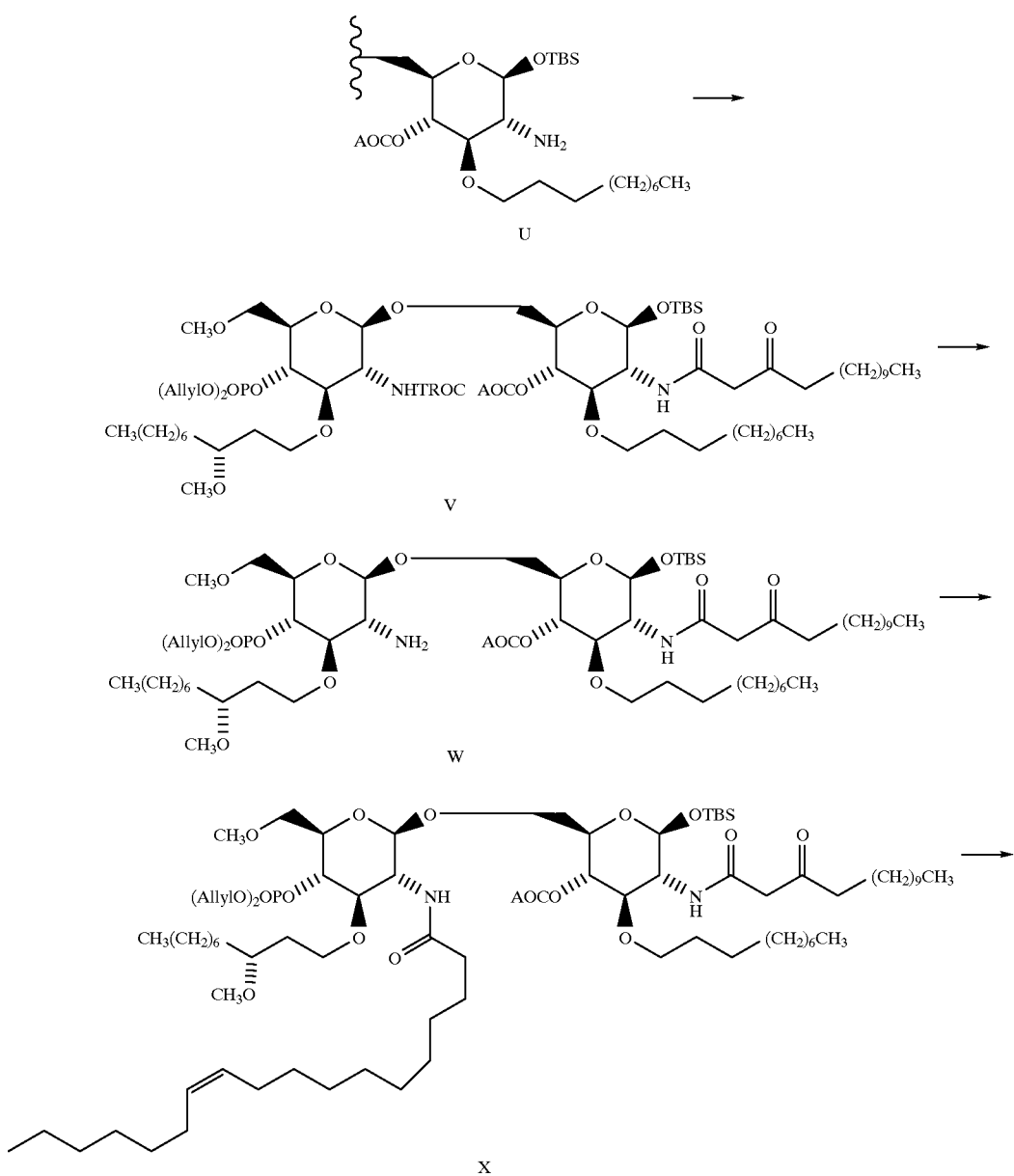

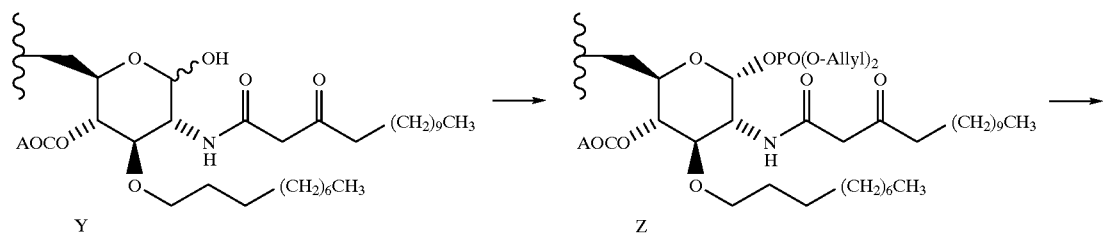

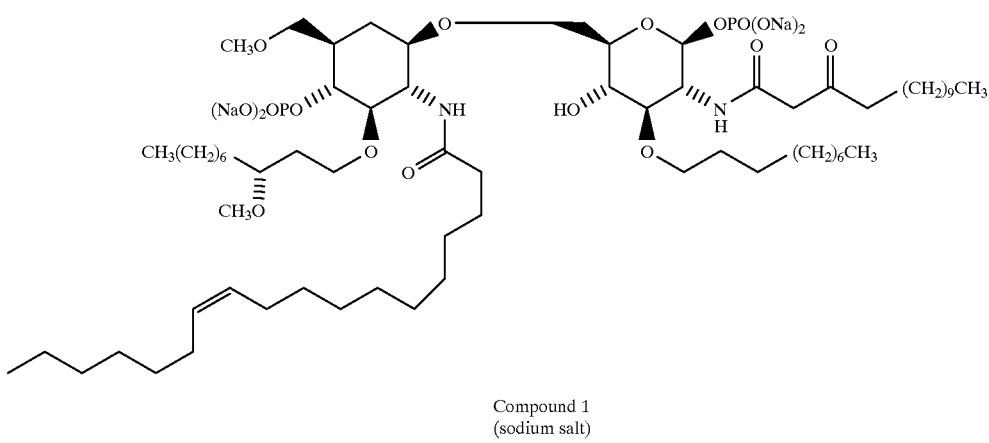

Compound 1
(sodium salt)

Formulations

Lipid A analogs are administered in dosages which provide suitable inhibition of LPS activation of target cells; generally, these dosages are, preferably between 0.01–50 mg/patient, more preferably, between 0.05–25 mg/patient and most preferably, between 1–12 mg/patient. Most preferably the dosages are administered over three days as a continuous infusion.

The term parenteral as used herein includes subcutaneous, intravenous, intramuscular, and intraarterial injections with a variety of infusion techniques. intraarterial and intravenous injection as used herein includes administration through catheters. Preferred for certain indications are methods of administration which allow rapid access to the tissue or organ being treated, such as intravenous injections for the treatment of endotoxemia.

Pharmaceutical compositions containing the active ingredient may be in any form suitable for the intended method of administration.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood, however, that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

EXAMPLES

Examples of use of the method of the invention includes the following. The compounds of this invention and their preparation can be understood further by the examples which illustrate some of the processes by which these compounds are prepared or used. These examples should not be construed as specifically limiting the invention and variations of the invention, now known or later developed, are considered to fall within the scope of the present invention as hereinafter claimed.

Compounds of the present invention are referred to by compound number to the tables below.

CHEMICAL EXAMPLES

Unless otherwise noted, all reactions were conducted under an inert atmosphere. Intermediates and final products gave spectral analysis (for example, nuclear magnetic resonance spectroscopy and/or mass spectroscopy) consistent with their proposed structures. Reactions were monitored by silica gel thin layer chromatography. Preparative chromatography, unless otherwise noted, was performed on silica gel.

Preparation of Compound 1 by Route 1

All sensitive reactions were run under nitrogen and in dry equipment and anhydrous sodium sulfate used as the drying agent unless otherwise specified. All products gave satisfactory nuclear magnetic resonance spectra.

Purification of

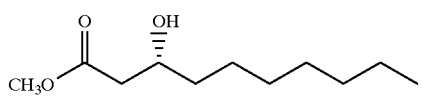

The material (5 kg) was chromatographed on silica and eluted with a gradient of hexane and EtOAc (100% to 33% hexane). The pure fractions were combined and distilled (97–100° C. at 0.15 mm Hg). Yield of purified material 4,513 g.

Formula 1

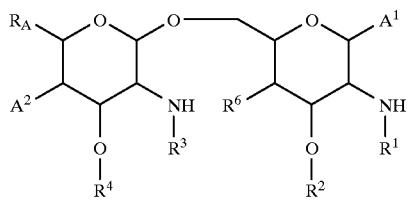

| Compound # | $A^1/A^2$ | $R^1$ | $R^2$ |
|---|---|---|---|
| 1 | $OPO(OH)_2$ | $COCH_2CO(CH_2)_{10}CH_3$ | $(CH_2)_9CH_3$ |
| 2 | $OPO(OH)_2$ | $COCH_2CO(CH_2)_{10}CH_3$ | $(CH_2)_9CH_3$ |
| 3 | $OPO(OH)_2$ | $COCH_2CO(CH_2)_{10}CH_3$ | $(CH_2)_9CH_3$ |
| 4 | $OPO(OH)_2$ | $COCH_2CHOH(CH_2)_{10}CH_3$ | $(CH_2)_9CH_3$ |
| 5 | $OPO(OH)_2$ | $COCH_2CO(CH_2)_{10}CH_3$ | $(CH_2)_9CH_3$ |
| 6 | $OPO(OH)_2$ | $CO(CH_2)_9CH=CH(CH_2)_5CH_3$ | $(CH_2)_9CH_3$ |
| 7 | $OPO(OH)_2$ | $CO(CH_2)_{12}CH_3$ | $(CH_2)_9CH_3$ |
| 8 | $OPO(OH)_2$ | $COCH_2CH(O\ CH_3)(CH_2)_{10}CH_3$ | $(CH_2)_9CH_3$ |
| 9 | $OPO(OH)_2$ | $COCH_2CH(O\ CH_3)(CH_2)_{10}CH_3$ | $(CH_2)_9CH_3$ |
| 10 | $OPO(OH)_2$ | $COCH_2CH(OH)CH_2)_{10}CH_3$ | $(CH_2)_9CH_3$ |
| 11 | $OPO(OH)_2$ | $COCH_2CO(CH_2)_{10}CH_3$ | $(CH_2)_9CH_3$ |

| Compound # | $R^3$ | $R^4$ | $R_A$ | $R^6$ |
|---|---|---|---|---|
| 1 | $CO(CH_2)_9CH=CH(CH_2)_5CH_3$ | $(CH_2)_2CH(O\ CH_3)(CH_2)_6CH_3$ | $CH_2OCH_3$ | OH |
| 2 | $CO(CH_2)_9CH=CH(CH_2)_5CH_3$ | $(CH_2)_2CH(OH)(CH_2)_6CH_3$ | $CH_2OCH_3$ | OH |
| 3 | $CO(CH_2)_{16}CH_3$ | $(CH_2)_2CH(OH)(CH_2)_6CH_3$ | $CH_2OCH_3$ | OH |
| 4 | $CO(CH_2)_9CH=CH(CH_2)_5CH_3$ | $(CH_2)_2CH(OH)(CH_2)_6CH_3$ | $CH_2OCH_3$ | OH |
| 5 | $CO(CH_2)_9CH=CH(CH_2)_5CH_3$ | $(CH_2)_9CH_3$ | $CH_2OCH_3$ | OH |
| 6 | $CO(CH_2)_9CH=CH(CH_2)_5CH_3$ | $(CH_2)_2CH(OH)(CH_2)_6CH_3$ | $CH_2OCH_3$ | OH |
| 7 | $CO(CH_2)_9CH=CH(CH_2)_5CH_3$ | $(CH_2)_2CH(OH)(CH_2)_6CH_3$ | $CH_2OCH_3$ | OH |
| 8 | $CO(CH_2)_9CH=CH(CH_2)_5CH_3$ | $(CH_2)_2CH(O\ CH_3)(CH_2)_6CH_3$ | $CH_2OCH_3$ | OH |
| 9 | $CO(CH_2)_9CH=CH(CH_2)_5CH_3$ | $(CH_2)_2CH(OH)(CH_2)_6CH_3$ | $CH_2OCH_3$ | OH |
| 10 | $CO(CH_2)_9CH=CH(CH_2)_5CH_3$ | $(CH_2)_2CH(O\ CH_3)(CH_2)_6CH_3$ | $CH_2OCH_3$ | OH |
| 11 | $CO(CH_2)_9CH=CH(CH_2)_5CH_3$ | $(CH_2)_2CH(O\ CH_3)(CH_2)_6CH_3$ | $CH_3$ | OH |

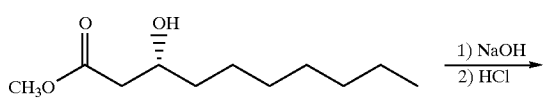

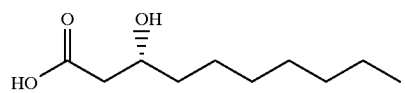

To an ice cold solution of the ester (4500 g, 22.2 moles) in 12.6 L of THF was added sodium hydroxide (27 moles) in 10.8 L of water. The mixture was stirred briefly and 2.5 L of conc hydrochloric acid was added. The layers were separated and the aqueous layer re-extracted with EtOAc. The combined organic layers were washed with brine, dried over sodium sulfate and concentrated. The product slowly crystallized to give 2983 g of white powder.

Purification of

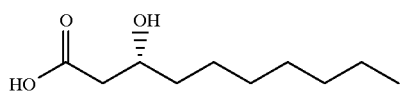

To a solution of the acid (15.8 moles) in 33 L of acetonitrile was added dicyclohexylamine (16.7 moles). The solution was heated to 60° C. and allowed to cool overnight. The crystals were collected and washed twice with solvent and recrystallized from acetonitrile. To a suspension of previously methanol washed Amberlite IR-120 Plus (12 kg) in EtOAc (24 L) and water (24 L) was added the above salt. The mixture was stirred for several hours and the organic layer separated. The aqueous layer was re-extracted with EtOAc (12 L) and the combined organic layers were dried (sodium sulfate) and concentrated to give 2,997 g of a white solid.

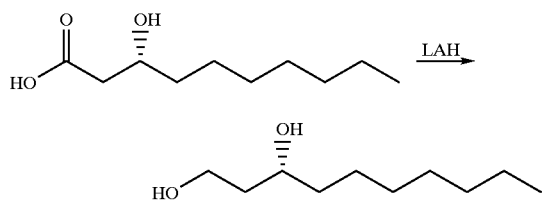

To a hot (~67° C.) 1M solution of lithium aluminum hydride (8 L) in THF was slowly added a solution of the acid (1 kg) in 4 L of THF. The solution was allowed to cool overnight. The solution was slowly added to 1M Aqueous HCl (5 L). The mixture was extracted with toluene (12 L). The organic layer was washed with sodium bicarbonate solution, dried (sodium sulfate) and the solvent removed under vacuum to give a syrup which was distilled (103° C.) to give 914 g of a light yellow oil.

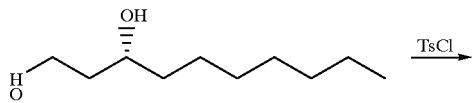

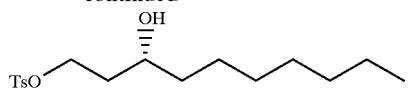

To a 0° C. solution of the diol (913.8 g) in pyridine (3 L) was added 3 L of triethylamine, followed by a solution of tosyl chloride (1 kg) in pyridine (1.5 L) and triethylamine (1.5 L). The mixture was allowed to warm overnight and poured onto a cold solution of 6M aqueous HCl (16 L) and methylene chloride (8 L). The organic layer was separated and the aqueous layer extracted with additional methylene chloride. The combined organic layers were dried (sodium sulfate) and the solvent removed under reduced pressure. The residue was chromatographed twice on silica and eluted with a gradient of hexane:EtOAc (9:1 to 1:6) to give 642 g of tosylate.

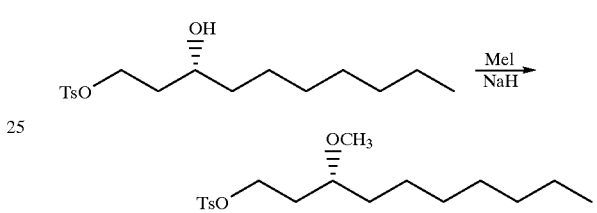

To a suspension of 60% sodium hydride oil dispersion (8.68 moles) in 1.15 L of DMF and 1.1 L of THF was slowly added the tosylate (1.139 kg) and methyl iodide (7.7 kg) in 1.15 L of DMF and 1.1 L of THF. The mixture was stirred overnight and then diluted with DMF (3 L) and slowly added to an satd aqueous solution of ammonium chloride. The mixture was extracted with hexane (8 L) which was dried (sodium sulfate) and the solvent removed to give a orange/brown oil. The oil was chromatographed on silica and eluted with a gradient (hexane:EtOAc 100:0 to 6:1) to give 940 g of a light yellow oil.

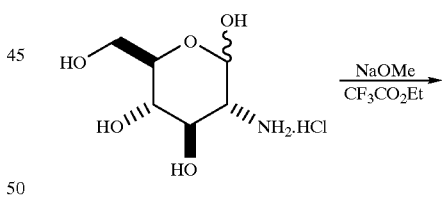

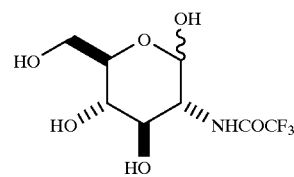

To a suspension of the aminosugar (1019 g) in 5 L of MeOH was added a 25% solution of NaOMe in MeOH (1080 mL, 5 moles), followed by 610 mL of ethyl trifluoroacetate. The mixture was stirred overnight and the solvent removed under reduced pressure and the residue titurated with isopropanol. The mixture was filtered and the residue washed with additional isopropanol to give 1369 g of product.

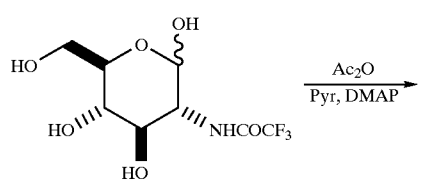

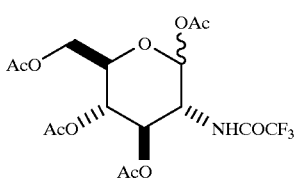

To a suspension of the hydroxy sugar (1300 g) in pyridine (4 L) was added dimethylaminopyridine (79 g), followed by acetic anhydride (2713 mL). The mixture was stirred overnight. The solvent was removed under reduced pressure. Toluene (5×500 mL) was added and also removed under reduced pressure to give a solid which was chromatographed on silica. Elution with hexane:EtOAc (1:1) gave 1479 g of a white solid.

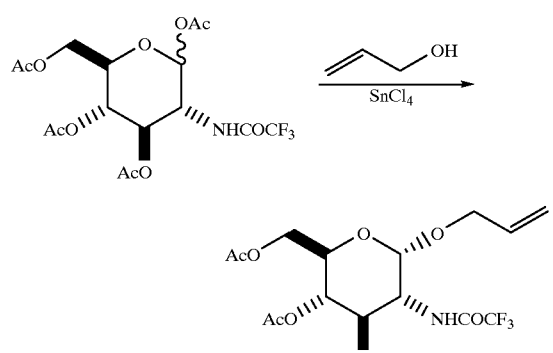

To a solution of the acetylated sugar (1479 g) in 8 L of methylene chloride was added allyl alcohol (764 mL), followed by slow addition of tin tetrachloride (976 mL). The mixture was stirred overnight and slowly poured onto ice cold water (7.5 L). The organic layer was separated and the aqueous layer washed with additional methylene chloride. The combined organic layers were washed with aqueous sodium bicarbonate, dried and concentrated under reduced pressure. The residue was chromatographed on silica (7.5 kg) and eluted with a hexane:EtOAc gradient (4:1 to 1:1) to give 1327 g of a pale yellow oil.

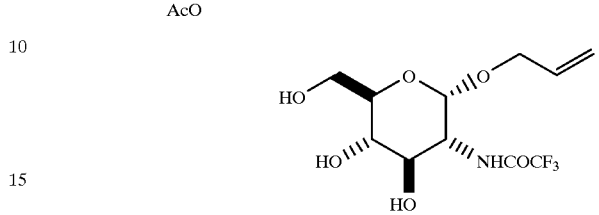

To a ice cold solution of protected sugar (1322 g) in 8.5 L of methanol was added to a 25% solution of NaOMe in methanol (437 mL) over one hour. To this was added previously washed 1740 g of Amberlite IR-120 Plus resin. The mixture was filtered, concentrated and the residue chromatographed on silica. Elution with methanol gave 907 g of product.

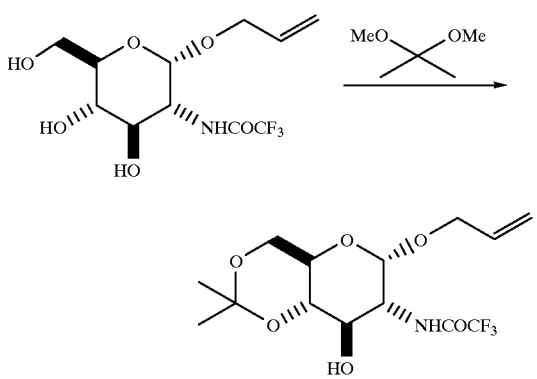

The triol was suspended in acetone (7.5 L) and camphorsulfonic acid (85 g) was added and then 2,2-dimethoxypropane (965 mL) was slowly added. The mixture was stirred overnight followed by the addition of triethylamine (51 mL). The solvent was removed under reduced pressure to give a brown solid which was chromatographed on silica. Elution with a hexane:EtOAc gradient (3:1 to 2:1) gave 842 g of a semi-white gum.

31

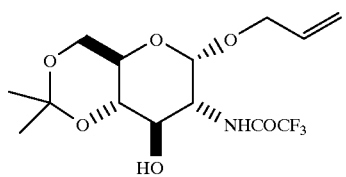

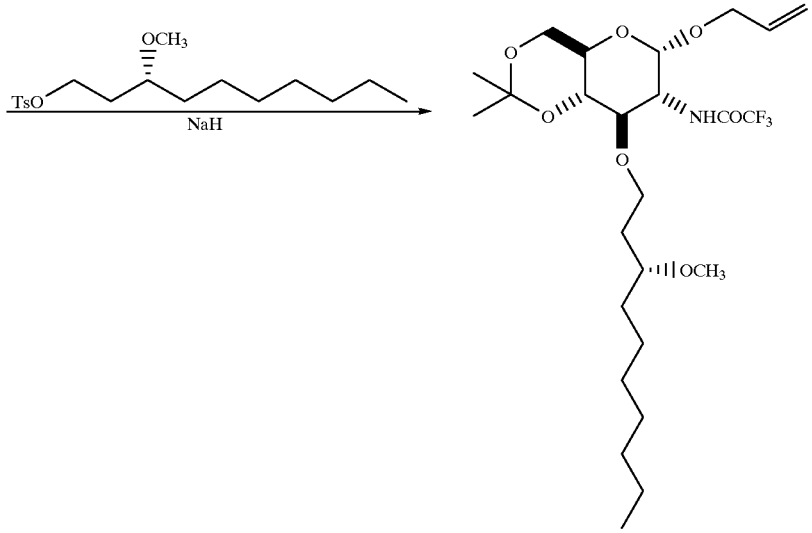

32

To a suspension of 60% sodium hydride oil dispersion (82 g) in 2.2 L of THF and 580 mL of DMF and was added the tosylate (351 g) and a solution of the free alcohol (400 g) in a mixture of 1360 mL of THF and 360 mL of DMF. The mixture was stirred overnight. The mixture was cooled in ice and methanol was added, followed by water (2 L). The mixture was extracted three times with EtOAc. The combined organic layers were dried and concentrated. The resulting mixture was chromatographed on silica. Gradient elution with hexane:EtOAc (19:1 to 1:1) gave 711 g.

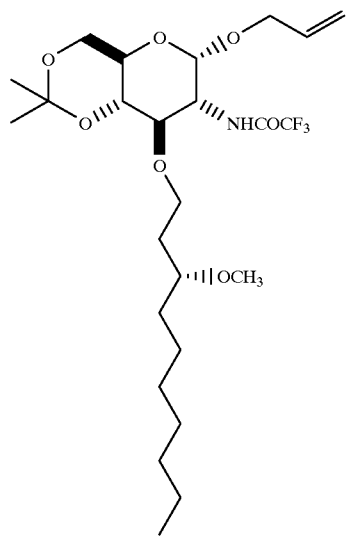

HF →

-continued

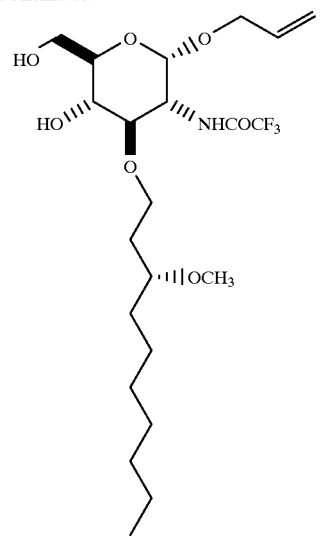

To a mixture of 48% aqueous hydrofluoric acid in 1500 mL of acetonitrile in a Teflon bottle was added a solution of the starting material (613 g) in 750 mL of acetonitrile and 750 mL of methylene chloride. The mixture was stirred for one hour and poured onto 8 L of water. The mixture was extracted with methylene chloride (4×2 L). The combined organic layers were washed with aqueous satd sodium bicarbonate solution, dried and concentrated under reduced pressure. The residue was chromatographed on silica. Gradient elution with methylene chloride:methanol (39:1 to 9:1) gave 519 g of product.

33

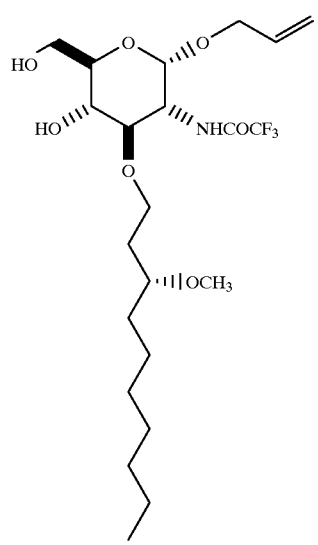

TsCl / Pyr, DMAP →

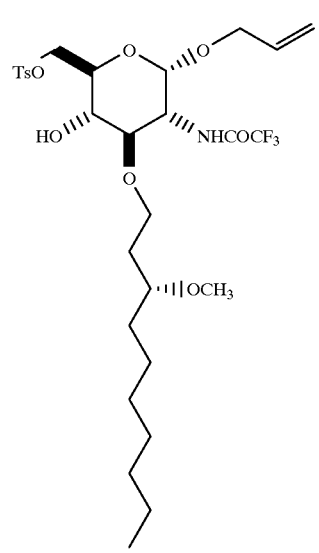

To a solution of the diol (577 g) in pyridine (5 L) was added tosyl chloride (339 g) and N,N-dimethylaminopyridine (14.5 g). The mixture was stirred at RT for two days and then poured onto 14 L of cold aqueous 1M hydrochloric acid. The mixture was extracted (2×5 L) with methylene chloride. The combined organic layers were dried and concentrated. The residue was chromatographed on silica. gradient elution (hexane:EtOAc, 6:1 to 1:1) gave 632 g of a yellow syrup which slowly crystallized on standing.

34

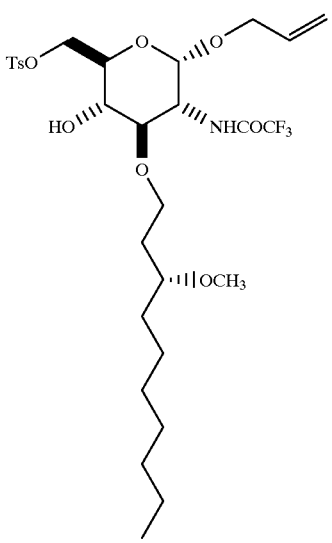

NaOMe →

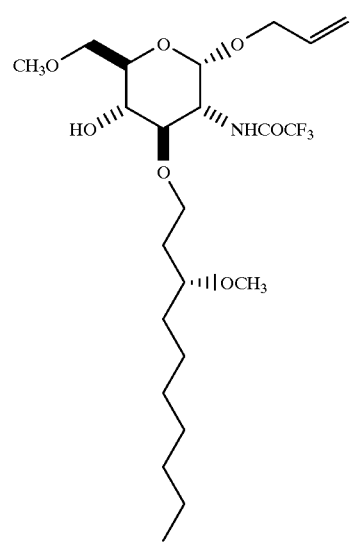

To an 85° C. solution of 25% sodium methoxide in methanol (1825 mL) in DMF (1365 mL) was added the tosylate (714 g) in DMF (1365 mL) over 1.25 hour. The mixture was stirred 30 minutes and cooled to 4° C. and poured onto an ice cold mixture of aqueous 1M hydrochloric acid and 4.6 kg of ice. The mixture was stirred for 30 minutes and filtered. The filtrate was washed with 2 L of water and the combined aqueous layers were extracted with 2×4 L of EtOAc. The combined organic layers were dried and concentrated. The residue was purified by chromatography on silica. Gradient elution (hexane:ethyl acetate 3:1 to 1:1) gave 549 g of a pale yellow to white solid.

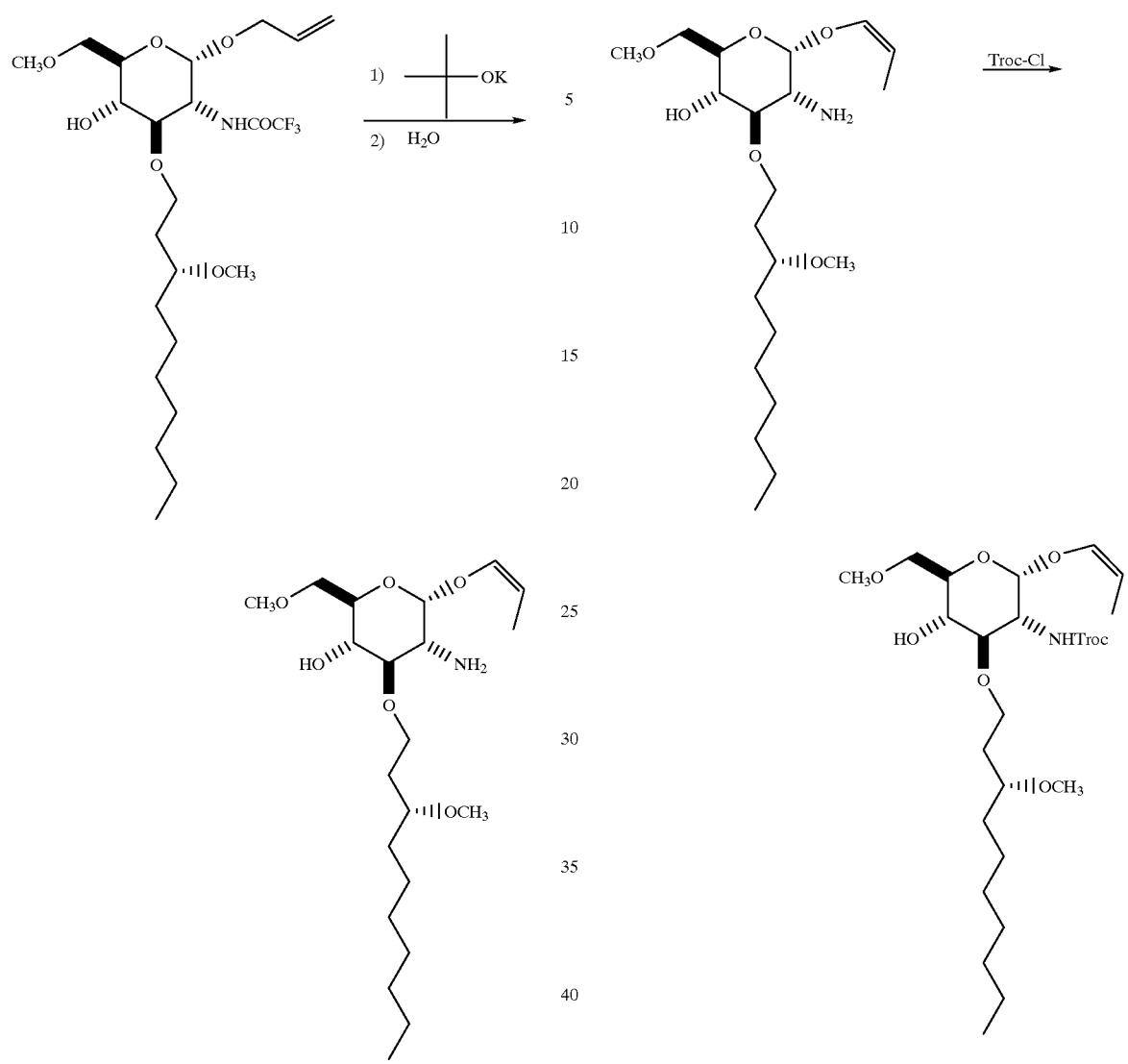

This reaction was run under argon. To a solution of potassium t-butoxide (139 g) in 440 mL of DMSO was added a solution of the sugar (247 g) in 440 mL of anhydrous DMSO. The mixture was heated to 85° C. for 1.5 hour and then 250 mL of water was added and the mixture heated overnight at 85° C. and cooled in an ice bath. The mixture was poured onto 3.5 L of brine and the mixture extracted with 3×750 mL of methylene chloride. The combined organic layers were dried and concentrated to yield 560 g of a brown oil.

To a mixture of the free amine (199 g) 780 mL of THF and 390 mL of satd aqueous sodium bicarbonate was added Troc-Cl (157 g). After ½ hour, the mixture was slowly poured onto a solution of 500 mL of 40% aqueous methylamine and 3 L of water. The mixture was extracted with 2×1750 mL of methylene chloride. The combined organic layers were dried and concentrated. The residue was chromatographed on silica. Gradient elution with hexane: EtOAc (5:1 to 1:1) gave a quantitative yield of 287 g of a yellow to off-white solid.

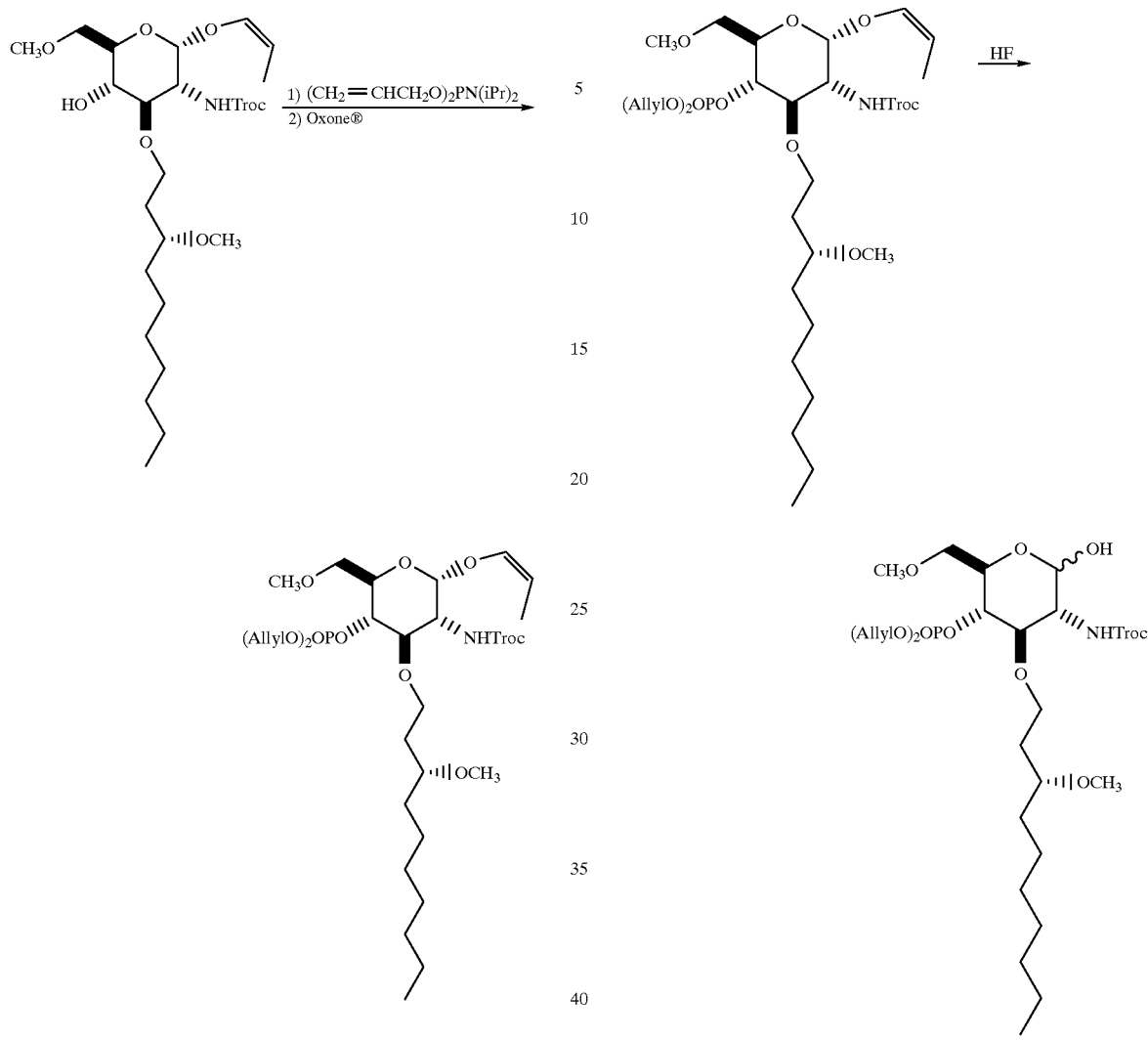

To a solution of the hydroxy-sugar in 2 L of methylene chloride was added tetrazole (155.6 g), followed by diallyi-diisopropylphosphoramidite (182 mL). After ½ hour, the mixture was poured onto an ice cold mixture of Oxone® (potassium peroxymonosulfate) (455.6 g), water (1.25 L) and THF (2.5 L). After 15 minutes, this mixture was poured onto cold 10% aqueous sodium thiosulfate. After 15 minutes, the mixture was extracted with 2 L of methylene chloride. The organic layer was separated, the aqueous layer re-extracted with methylene chloride and the combined organic layers dried and the solvent removed under vacuum. The residue was chromatographed on silica. Gradient elution with hexane/ethyl acetate (6:1 to 2:1) gave 205.7 g of pale yellow syrup.

To a solution of 48% aqueous hydrofluoric acid, 400 mL, in acetonitrile, 1.2 L in a Teflon container was added a solution of the sugar, 138.8 g, in methylene chloride, 500 mL. The mixture was stirred overnight, diluted with water, 3 L, and extracted with methylene chloride, 2.4 L. The organic layer was washed with aqueous sodium bicarbonate solution, dried and the solvent was removed under reduced pressure. The residue was chromatographed on silica. Gradient elution (hexane:ethyl acetate 2:1 to 1:1), followed by elution with a gradient of methylene chloride: methanol (19:1 to 9:1) gave 129.2 g as a waxy gum.

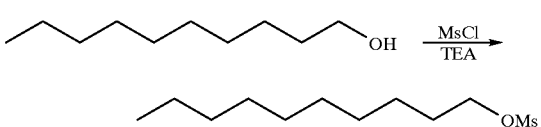

To a ice cold solution of 450 g of 1-decanol in 685 mL of triethylamine and 1125 mL of methylene chloride was added 330 mL of mesyl chloride. The cooling bath was removed after 1½ hour and the solvent removed under reduced pressure. To the residue was added 2.5 L of 1M aqueous hydrochloric acid. This mixture was extracted 3×2 L of methylene chloride. The organic layers were combined, dried and the solvent removed under reduced pressure. The residue was chromatographed on silica. Elution with 1:1 hexane:ethyl acetate gave 651 g of product.

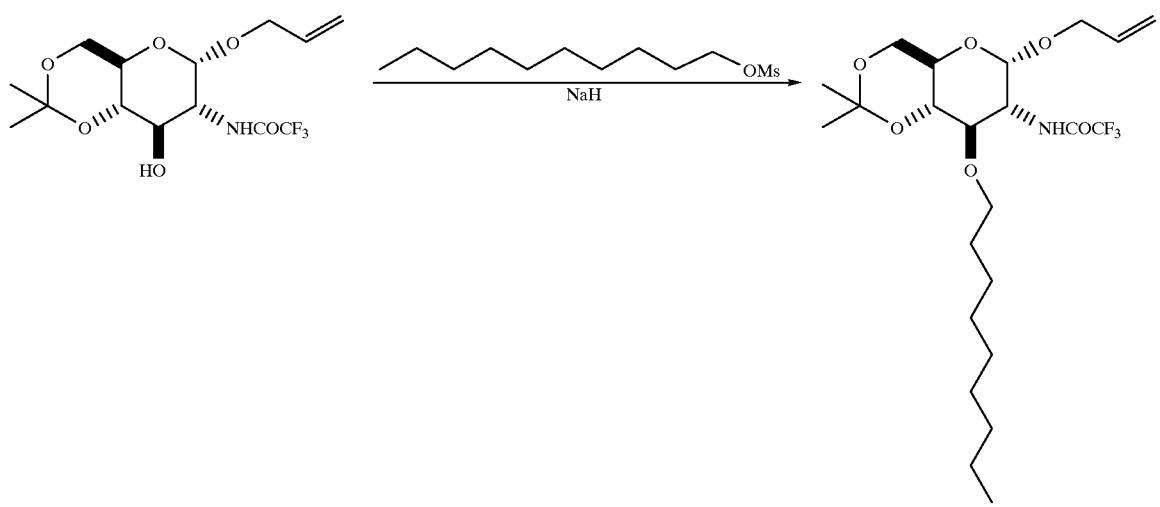

To a suspension of 60% sodium hydride mineral oil dispersion in 1 L of THF and 470 mL of DMF was added a solution of the alcohol in 280 mL of DMF and 1 L of THF over 1 hour. The mesylate, 470 g, was then added over 15 minutes. After 2 days, 400 mL of methanol was added, followed by 4 kg of ice and 4 L of water. This mixture was extracted with 2×4 L of ethyl acetate. The combined organic layers were dried and the solvent was removed under reduced pressure. The residue was chromatographed on silica. Gradient elution with hexane:EtOAc (39:1 to 2:1) gave 618 g.

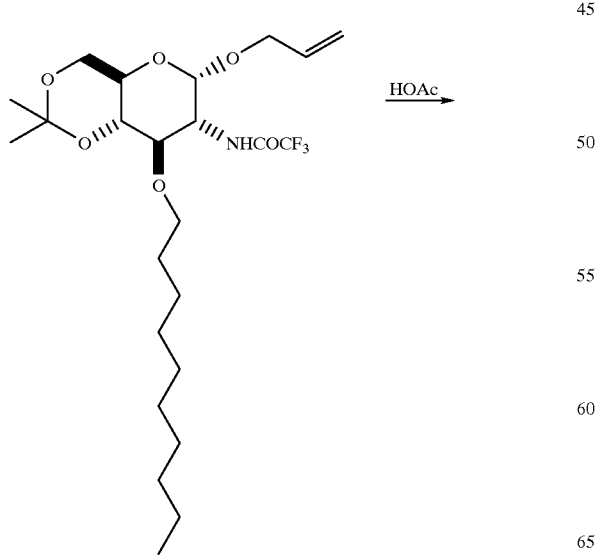

-continued

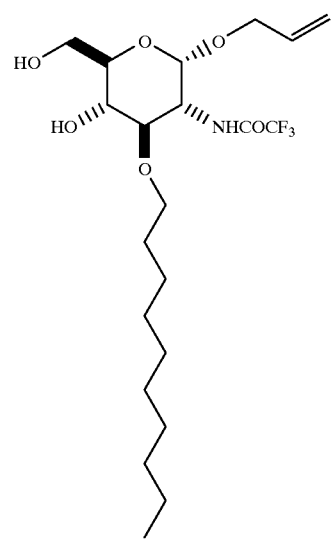

A solution of the sugar, 520 g, in 5.2 L of glacial acetic acid and 1.3 L of water was stirred overnight. It was poured onto 7.5 L of water and filtered. The filtrate was dried by azeotropic distillation with toluene (3×500 mL) under reduced pressure to give 458 g.

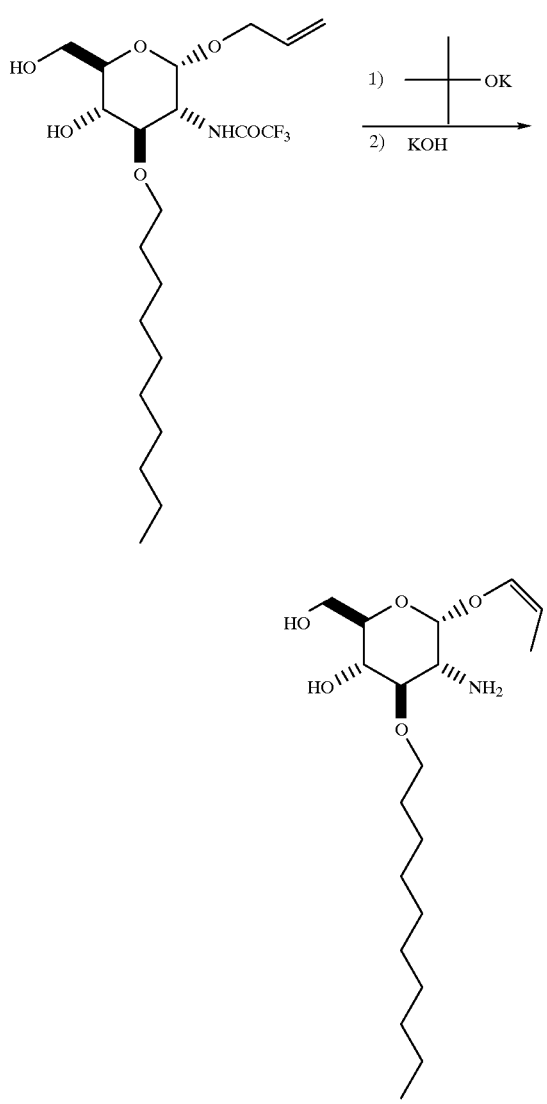

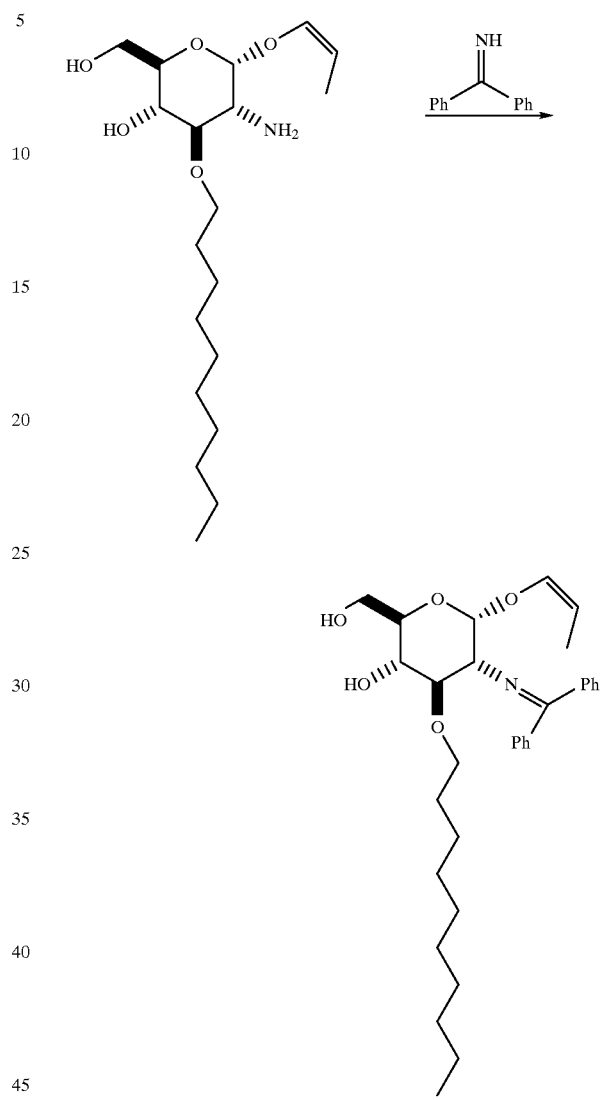

This reaction was run under argon. To a suspension of potassium t-butoxide, 295 g, in DMSO, 1 L, was added a solution of 340 g of the sugar in 1.5 L of DMSO. The mixture was heated to 85° C. for 1¼ hour and 1.4 L of 3M aqueous potassium hydroxide was added and the mixture stirred overnight at 85° C. The mixture was cooled to room temperature and poured onto a mixture of 3.5 L of brine and 3.5 L of water. The mixture was extracted three times with methylene chloride, the mixture dried and the solvent was removed under reduced pressure. The residue was chromatographed on silica. gradient elution with methylene chloride:methanol 19:1 to 4:1) gave 740 g of product.

A solution of the aminosugar, 740 g, in benzophenone imine, 338 g, was heated at 45° C. overnight. The mixture was chromatographed on silica and eluted with a gradient of hexane/ethyl acetate (39:1 to 1/1) to give 371 g of a pale yellow solid.

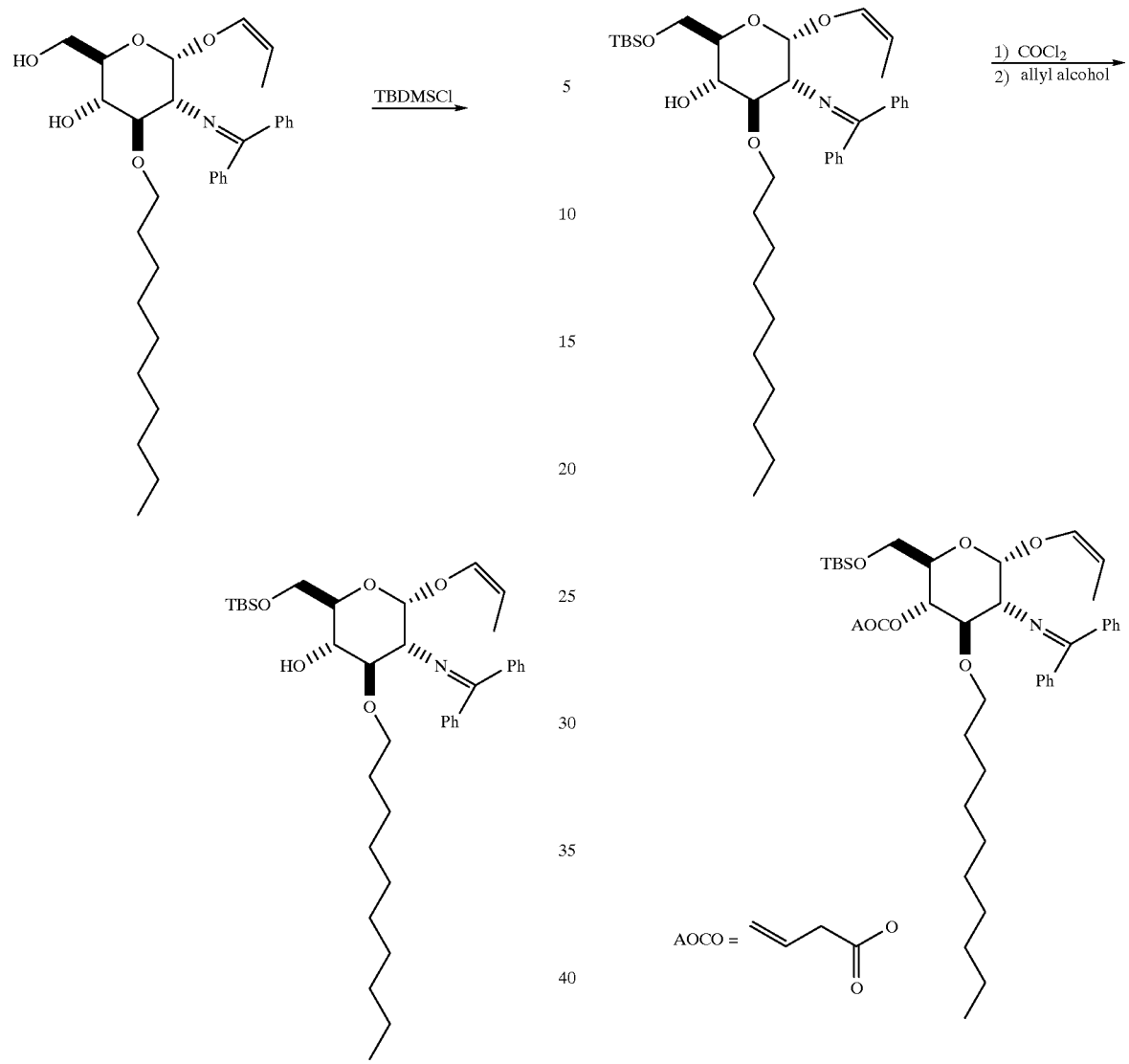

To a solution of the diol sugar, 366 g, in 1.3 L of DMF was added imidazole, 118 g, followed by t-butyldimethylsilyl chloride, 117 g. After 5 minutes, the mixture was poured onto 1.4 L of aqueous saturated sodium bicarbonate. The mixture was extracted with ethyl acetate three times. The organic layers were combined, the solvent was removed under reduced pressure and the residue chromatographed on silica. Gradient elution with hexane/ethyl acetate (49:1 to 4:1) gave 446 g of a syrup.

To a solution of the alcohol, 437 g, in toluene, 3 L, was added pyridine, 225 mL and the solution cooled in an ice bath. Phosgene, 531 mL of a 1.9M solution in toluene was added and the solution stirred for 10 minutes. Allyl alcohol, 469 mL, was added. After 40 minutes, saturated aqueous sodium bicarbonate solution, 2.3 L, was added and the mixture extracted with ethyl acetate. The organic layer was separated, dried and the solvent was removed under reduced pressure. The residue was chromatographed on silica. Gradient elution with hexane/ethyl acetate (49:1 to 4:1) gave 441 g of yellow syrup.

45

46

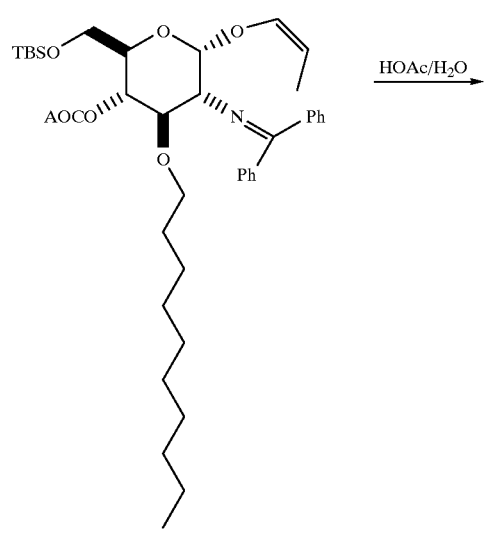

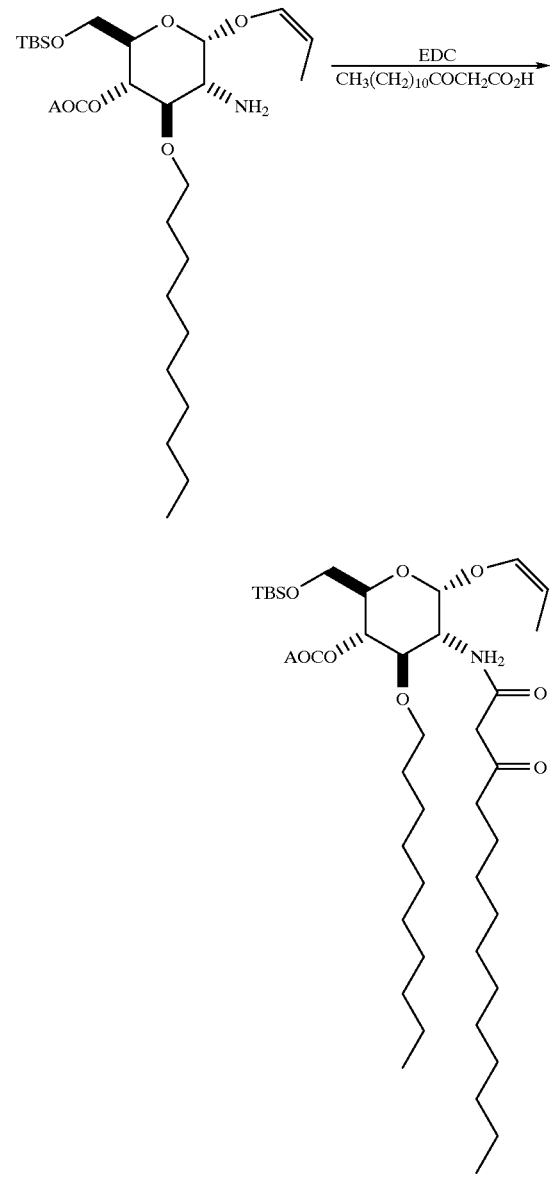

To a solution of the sugar, 431 g, in THF, 200 mL, was added glacial acetic acid, 330 mL, and water, 110 mL. The mixture was stirred for three hours, cooled in ice and 6.6 L of 1M aqueous sodium hydroxide was added. The mixture was extracted with methylene chloride, 2×2 L. The combined organic layers were dried and the solvent was removed under reduced pressure. The residue was chromatographed on silica. Gradient elution with methylene chloride:methanol (19:1 to 4:1) gave the amine, 309 g as a syrup.

To a ice cold solution of the amino sugar, 309 g, in 3 L of methylene chloride was added 1-(3-dimethylaminopropyl)-3-ethylcarbodiimide hydrochloride (EDC), 435 g, followed in 10 minutes by the carboxylic acid, 275 g. After 10 minutes, the mixture was extracted with saturated aqueous sodium bicarbonate. The organic layer was separated, the aqueous layer re-extracted with methylene chloride, the combined organic layers dried and the solvent was removed under reduced pressure. The residue was chromatographed on silica. Gradient elution (hexane:ethyl acetate 19:1 to 3:1) gave 338 g of pale yellow syrup.

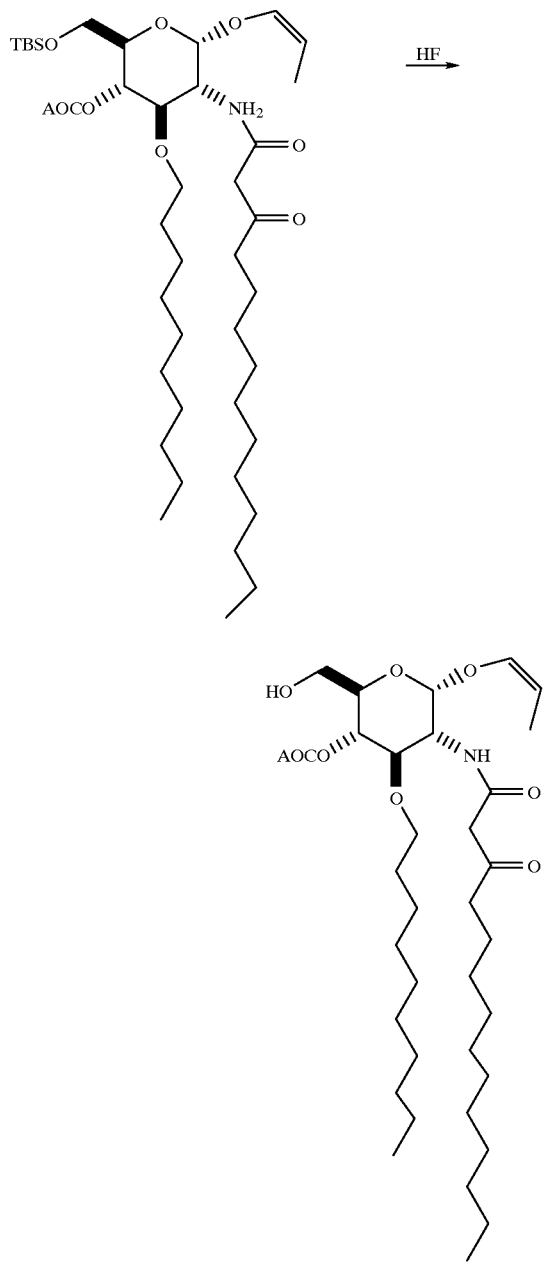

To a solution of 48% aqueous hydrofluoric acid, 11 mL, in acetonitrile 293 mL, was added 4.6 g of silica gel, followed by a solution of the sugar, 146.7 g, in methylene chloride, 147 mL. After one half hour, the mixture was diluted with water, 975 mL, and extracted with methylene chloride. The organic layer was separated and the aqueous layer re-extracted with methylene chloride. The combined organic layers were washed with aqueous sodium bicarbonate solution, dried and the solvent was removed under reduced pressure. The residue was chromatographed on silica. Gradient elution (hexane:ethyl acetate 5:1 to 0:1) gave 110.4 g of an off-white waxy solid.

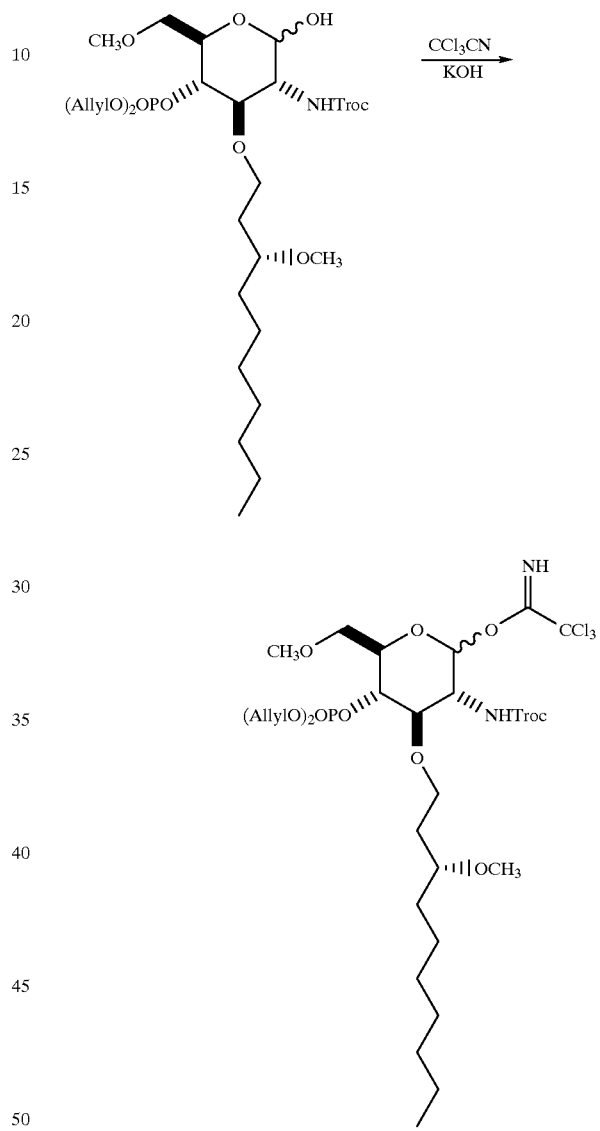

To a solution of the sugar, 129 g, in 500 g of trichloroacetonitrile was added potassium carbonate, 240 g. The mixture was stirred for one half hour and filtered through diatomaceous earth. The filter cake was washed with methylene chloride and the filtrates combined and the solvent was removed under reduced pressure. The residue was chromatographed on silica. Gradient elution (hexane:ethyl acetate 1:1 to 0:1) gave 145.7 g of a yellow gum.

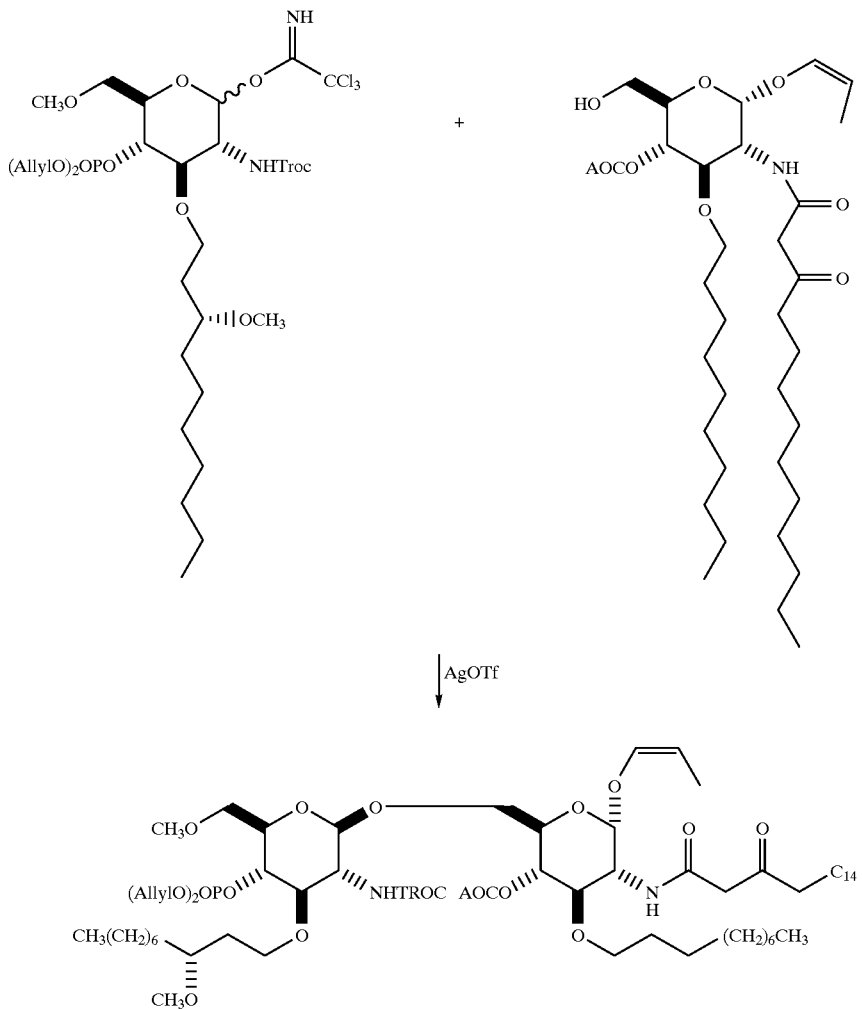

The left sugar, 145.7 g, and of the right sugar, 109.2 g, were azetropically dried by evaporating toluene (3×200 mL). A solution of the two sugars in 750 mL of methylene chloride was added to an ice cold solution of silver triflate, 62.7 g in 130 mL of methylene chloride. The mixture was warmed to room temperature and stirred overnight. The mixture was poured onto a mixture of saturated aqueous sodium bicarbonate and sodium thiosulfate solution. The organic layer was separated and the aqueous layer washed with methylene chloride. The combined organic layers were dried and the solvent was removed under reduced pressure. The residue was chromatographed twice on silica. Gradient elution with hexane:ethyl acetate (5:1 to 1:1) gave 189.56 g of a sticky foam.

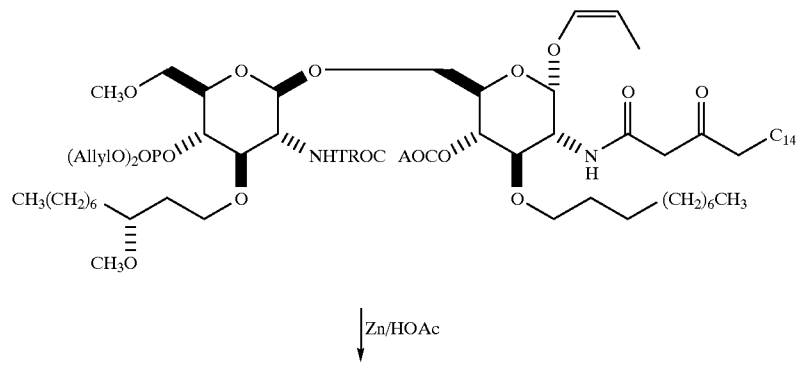

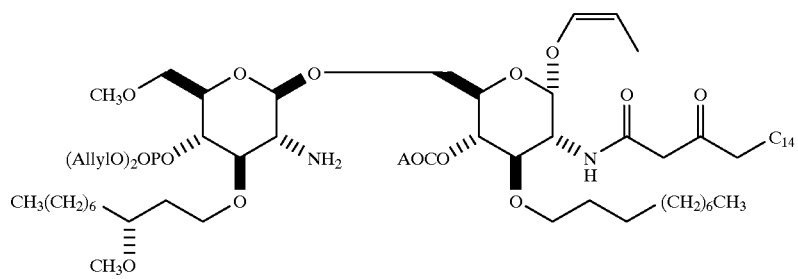

To a solution of the disaccharide, 188.7 g, in THF, 590 mL, was added zinc dust, 457.6 g, followed by glacial acetic acid, 395 mL. After one half hour, the mixture was filtered through diatomaceous earth and the filter cake washed with THF. The organic layers were combined and the solvent was removed under reduced pressure. The residue was dried azeotropically by distilled benzene from the residue (4×250 mL) to give 223.1 g of a pink gum.

of water. cis-11-Octadecenoyl chloride, 67.4 g, was added. After 10 minutes, the mixture was extracted twice with ethyl acetate. The combined organic layers were dried and the solvent was removed under reduced pressure. The residue was chromatographed on silica. Gradient elution with hexane:ethyl acetate (2:1 to 0:1) gave 160.2 g of pale yellow wax.

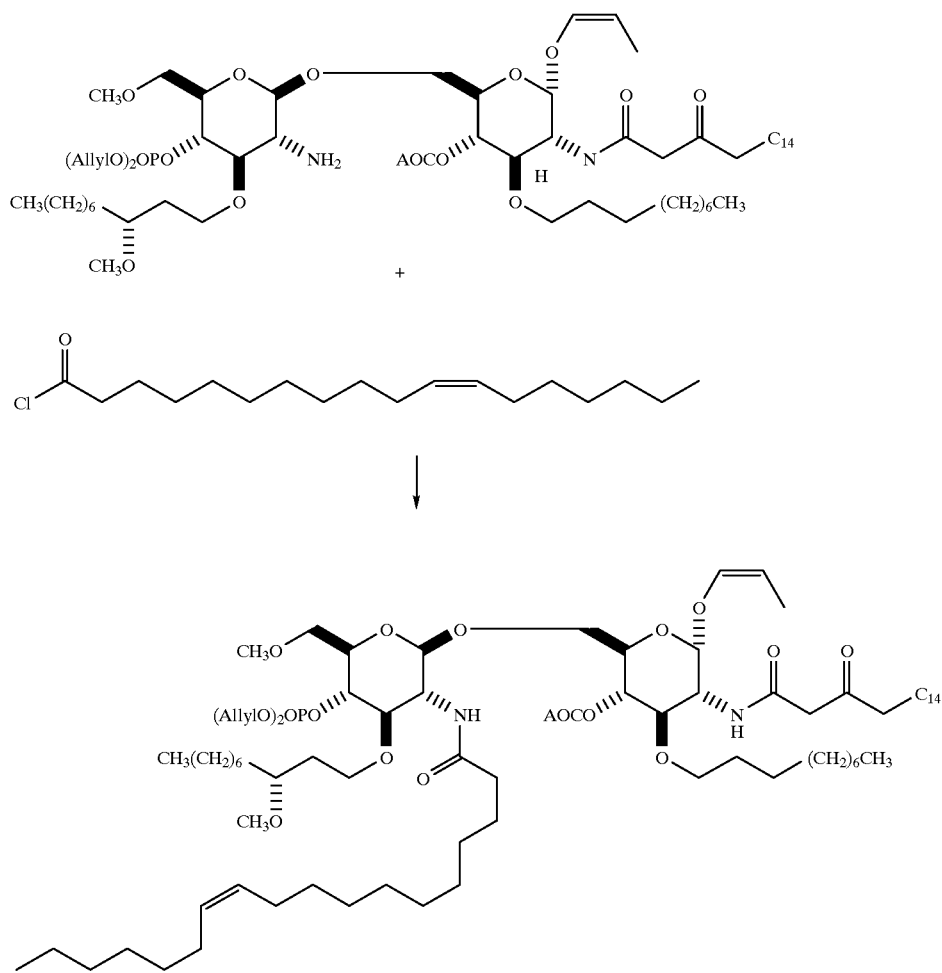

To a solution of the sugar, 223.1 g, in 1.3 L of THF was added a solution of sodium bicarbonate, 37.5 g, in 250 mL

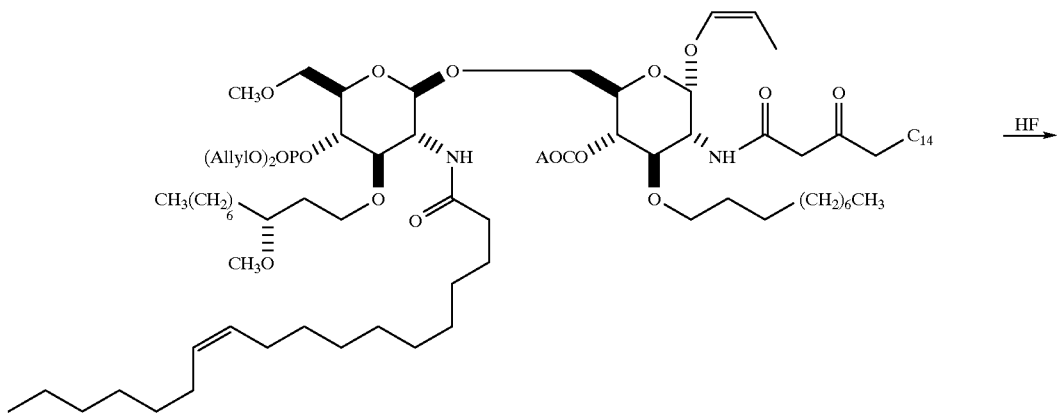

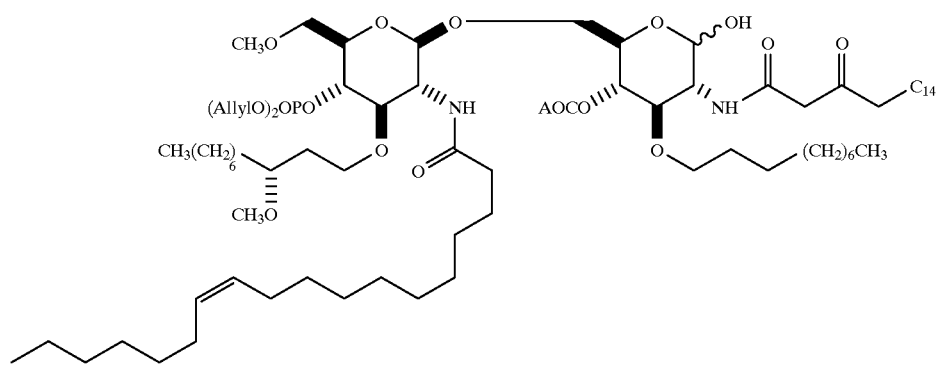

A solution of the sugar, 161.3 g, in methylene chloride, 215 mL, in a Teflon bottle was added to a solution of 48% hydrofluoric acid, 150 mL, in acetonitrile, 474 mL. After four hours, the mixture was poured onto 500 mL of water. The mixture was extracted twice with methylene chloride. The combined organic layers were washed with aqueous saturated sodium bicarbonate, dried and the solvent was removed under reduced pressure. The residue was chromatographed on silica. Gradient elution (methylene chloride:ethyl acetate:methanol 500:500:20 to 500:500:160) gave a yellow waxy gum.

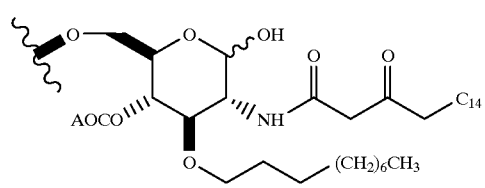

Phosphorylation

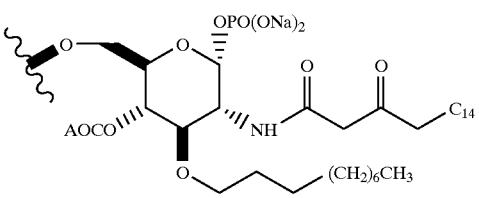

The sugar, 719 mg, was dissolved in methylene chloride and sodium sulfate (1.4 g) was added. Diallyidiiospropylphosphoramidite (189 μL) and tetrazole (162 mg) were added, the mixture stirred for 10 minutes and then cooled to −78° C. A solution of m-chloroperoxybenzoic acid (192 mg) in methylene chloride (4 mL) was added dropwise. The mixture was washed with aqueous sodium thiosulfate and with aqueous sodium bicarbonate, dried (sodium sulfate) and the solvent removed under reduced pressure. The residue was chromatographed to give 660 mg.

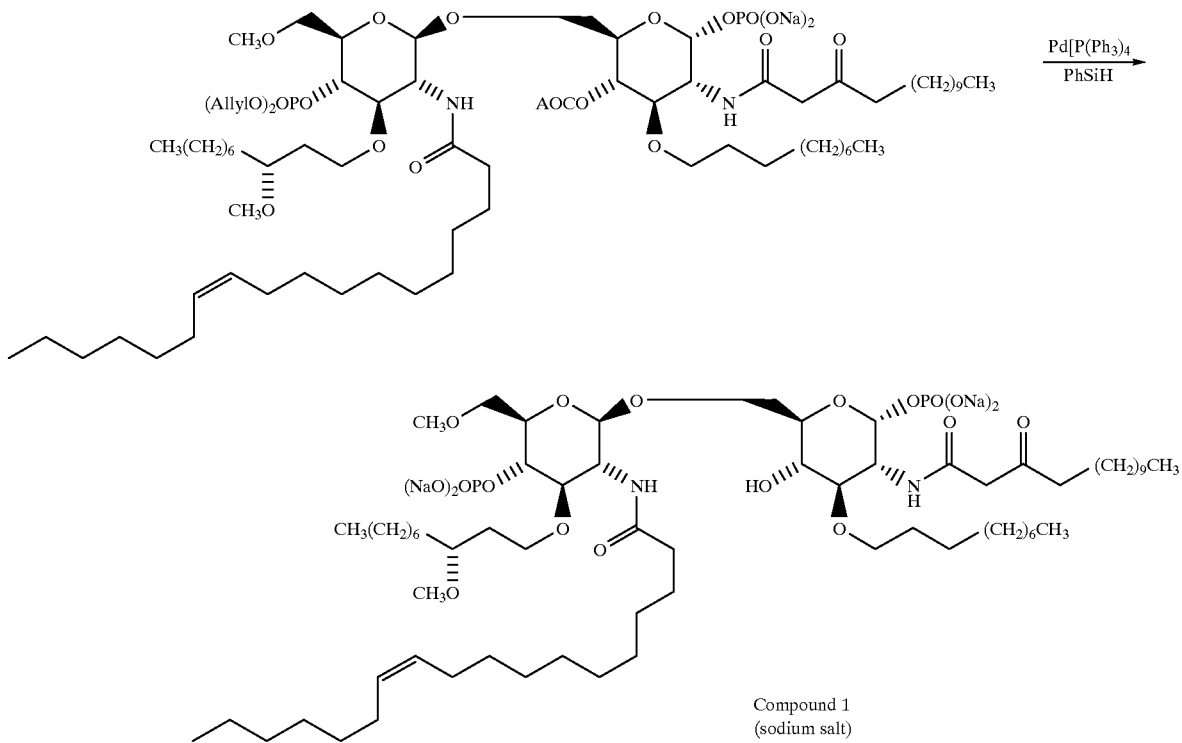

Compound 1
(sodium salt)

To a solution of tetrakis(triphenylphosphine)palladium (0) (166 mg) in 2 mL of tetrahydrofuran: acetic acid (10:1) mixture was added a solution of intermediate Z (660 mg) in 3 mL of the same solvent mixture. After 30 minutes, additional tetrakis(triphenylphosphine)palladium (0) was added. After an additional 1½ hours, toluene was added and the solvent removed under reduced pressure. The mixture was purified by chromatography on diethylaminoethylcellulose. The purified mixture was dissolved in 0.1N aqueous sodium hydroxide, filtered through a 0.45 µ sterile filter and purified by HPLC on a YMC-Pack ODS-AP column to give 130 mg of compound 1.

Analytical data for compound 1 made by the methods described above is given below:

Compound 1: $^1$H NMR (CD$_3$OD) δ: 5.3 (1H, m), 4.6 (1, m), 4.0 (m, m), 3.9 (1H, d), 3.7 (1H, t), 3.6 (1H, t), 3.4 (3H, s), 3.3 (3H, t), 2.6 (2H, t), 2.3 (2H, m), 2.0 (2H, m), 1.7–1.2 (m, m), 0.9 (6H, t).

$^{31}$P NMR (CD$_3$OD) δ: 4.71, 3.98.

Preparation of Compound 1 by Route 2

Preparation of Compound 1

Example 1

Intermediate B

To a suspension of intermediate A (15 g), prepared by the method of Christ, et al., European patent application 92309057.5, in CH$_2$Cl$_2$ (150 mL) and 48% HBF$_4$ (29.2 g), cooled via ice-bath, was added TMSCHN$_2$ (165 mL as a 2M solution in hexane). The mixture was stirred until the reaction was almost complete by TLC and then methanol (20 mL) was added followed by acetic acid (10 mL). Aqueous sodium bicarbonate was added and the mixture extracted with methylene chloride. The mixture was dried (sodium sulfate) and the solvent removed under reduced pressure. Chromatography of the residue gave B, 14.9 g.

Example 2

Intermediate C

To a cold (0° C.) solution of B (14.9 g) in methylene chloride (100 mL) was slowly added diisobutylaluminum hydride (140 mL as a 1M solution in hexanes) until reaction was complete as determined by TLC. The reaction was quenched by the addition of aqueous 1N hydrochloric acid (100 mL) followed by conc. hydrochloric acid (50 mL). The layers were allowed to separate and the aqueous layer was re-extracted with CH$_2$Cl$_2$. The combined organic layers were then washed with brine, dried over sodium sulfate and concentrated under reduced pressure. After purification by silica chromatography, 12.06 g of intermediate C was obtained.

Example 3

Intermediate D

To a solution of C (10.64 g) in methylene chloride (40 mL) was added triethylamine (15.75 mL), p-toluenesulfonyl chloride (11.86 g) and dimethylaminopyridine (690 mg). The resulting suspension was allowed to stir until reaction was complete as determined by TLC then quenched via water work-up with methylene chloride extraction. After purification by silica chromatography, 18.7 g of D was obtained.

Example 4

Intermediate E

To a solution of D (18.7 g) in 200 mL of acetone was added sodium iodide (24.6 g). The mixture heated at reflux for 1½ hours, the solvent removed under reduced pressure and the residue partitioned between water and hexane. The organic layer was separated, dried (sodium sulfate) and the solvent removed. Chromatography (silica) gave 15.4 g of E as a colorless liquid.

Example 5
Intermediate F

This compound was prepared by the method of Christ, et al., European Patent Application 92309057.5.

Example 6
Intermediate G

To a solution of 18.6 g of intermediate F and 15.4 g of intermediate E in hexane was added 23.9 g of silver oxide and the mixture refluxed overnight. The mixture was cooled, filtered through diatomaceous earth, the solvent removed and the residue chromatographed (silica) to give intermediate G (21 g) as a colorless syrup.

Example 7
Intermediate H

To a cold (0° C.) solution of intermediate G (21 g) in methylene chloride was added dropwise 3.5 mL of 48% tetrafluoroboric acid. After 5 minutes, the mixture was washed with aqueous sodium bicarbonate solution and with brine. The mixture was concentrated under reduced pressure and chromatographed (silica) to give intermediate H, 18.7 g, as a colorless syrup.

Example 8
Intermediate I

To a solution of intermediate H (17.6 g) in neat methyl iodide (105 mL) was added silver oxide (83 g). The mixture was stirred overnight and then diluted with hexane and filtered through diatomaceous earth. The mixture was concentrated under reduced pressure and the residue dissolved in methylene chloride (40 mL). The mixture was cooled to 0° C. and to it was added imidazole (2.44 g) and t-butyldimethylsilyl chloride (4.7 mL). It was stirred overnight and 150 mL of sodium bicarbonate solution was added. The organic layer was dried (sodium sulfate) and chromatographed (silica) to give intermediate I, 10.5 g, as a colorless syrup.

Example 9
Intermediate J

Intermediate I was dissolved in 100 mL of methylene chloride to which as added diallyldiisopropylphosphoramidite (7.4 mL), followed by tetrazole (6.37 g). The mixture was cooled and stirred for 20 minutes. A suspension of metachloroperoxybenzoic acid (24.2 mmol) in 50 mL of methylene chloride was added over 15 minutes while the temperature of the reaction was maintained below −60° C. Sodium bicarbonate solution was added and the organic layer separated, dried (sodium sulfate) and the solvent removed under reduced pressure. Chromatography (silica) gave 14 g of a colorless syrup of intermediate J.

Example 10
Intermediate K

To a suspension of 39.5 g of di(thiophenyl)tin (prepared by the method of Christ, et al., European patent application 92309057.5) in 235 mL of methylene chloride was added thiophenol (12 mL). To this mixture was added triethylamine dropwise over 15 minutes. A portion (150 mL) of this "tin reagent" mixture was added dropwise over 15 minutes to a solution of intermediate J (12.9 g) in 25 mL of methylene chloride. The remainder of the "tin reagent" was added over 30 minutes to drive the reaction to completion. The mixture was diluted with ethyl acetate and washed with aqueous 1N sodium hydroxide and with brine. The organic layer was dried (sodium sulfate), the solvent removed and the residue chromatographed to give 11.1 g of a yellow syrup, intermediate K.

Example 11
Intermediate L

To a cold solution of intermediate K (11.1 g) and pyridine (7.1 mL) in 80 mL of methylene chloride was added trichloroethyl chloroformate (2.9 mL) and the mixture was stirred overnight. Aqueous sodium bicarbonate solution was added, the organic layer was separated, dried (sodium sulfate) and the solvent removed under reduced pressure. Chromatography gave intermediate L, 12.96 g as light yellow solid.

Example 12
Intermediate M

Intermediate L, 12.96 g, was dissolved in methylene chloride. To this mixture was added a 6M solution of hydrogen fluoride in acetonitrile and the mixture stirred for 4 hours. Aqueous sodium bicarbonate solution was added the organic layer separated, dried (sodium sulfate) and the solvent removed under reduced pressure. Chromatography gave 10.9 g of an amber syrup, intermediate M.

Example 13
Intermediate N

To a solution of intermediate M (9.5 g) in 50 mL of trichlororacetonitrile was added potassium carbonate (15 g) and the mixture stirred for 10 minutes. The mixture was filtered through diatomaceous earth and the solvent removed under reduced pressure. Chromatography gave 14.5 g, intermediate N which was used at once in Example 19.

Example 14
Intermediate O

To a solution of intermediate F (160 g) in hexane (475 mL) and iododecane (474 mL) was added silver oxide (723 g). The mixture was heated at 70° C. in the dark for 2 hours and filtered through diatomaceous earth. The solution was concentrated under reduced pressure and the residue chromatographed to give 221 g of intermediate O as a colorless oil.

Example 15
Intermediate P

To a solution of intermediate O (30 g) in methylene chloride (90 mL) and acetonitrile (90 mL)was added a solution of 48% aqueous hydrogen fluoride (9 mL) in acetonitrile (81 mL). The mixture was stirred for 30 minutes and 350 mL of aqueous sodium bicarbonate was added. The mixture was extracted with methylene chloride. The organic layer was dried (sodium sulfate), the solvent removed under reduced pressure and the residue chromatographed to yield 30 g of intermediate P as a yellow oil.

Example 16
Intermediate Q

To a cold (0° C.) solution of intermediate P (30 g) and imidazole (10.2 g) in methylene chloride (500 mL) was added t-butyldimethylsilyl chloride (10.85 g). The mixture was stirred for 1½ hours and then poured onto 400 mL of saturated aqueous ammonium chloride. The organic layer was separated, dried (sodium sulfate), the solvent removed under reduced pressure and the residue chromatographed to give 34.5 g of intermediate Q as a colorless syrup.

Example 17
Intermediate R

To a cold (0° C.) solution of intermediate Q (32.2 g) and pyridine (184 mL) in toluene (213 mL) was added a 1.94M solution of phosgene in toluene. After 20 minutes, allyl alcohol (31 mL) was added and the mixture stirred for 30 minutes. Aqueous sodium bicarbonate was added, the organic layer separated, dried (sodium sulfate) and the solvent removed under reduced pressure. Chromatography gave 36.9 g of intermediate R as a colorless syrup.

Example 18

Intermediate S

To a solution of 2.4 mL of 48% aqueous hydrogen fluoride in 48 mL of acetonitrile was added a solution of intermediate R (20 g) in methylene chloride (24 mL) and the mixture stirred overnight. Aqueous sodium bicarbonate solution was added, the organic layer separated and dried (sodium sulfate) and the solvent removed under reduced pressure. Chromatography yielded 11 g of intermediate S as a colorless syrup.

Example 19

Intermediate T

Intermediate S (8.97 g) and intermediate N (14.5 g) were dissolved in toluene (20 mL) and the mixture dried by azeotropic removal of the solvent. This procedure was repeated three times. The dried mixture was dissolved in 50 mL of methylene chloride which was slowly added to a solution of silver triflate (5.8 g) in 50 mL of methylene chloride. The mixture was stirred for 10 minutes and 250 mL of aqueous sodium bicarbonate solution and 250 mL of 10% aqueous sodium thiosulfate was added. The organic layer was separated, dried (sodium sulfate) and the solvent removed under reduced pressure. Chromatography gave 13 g of intermediate T as a pale yellow syrup.

Example 20

Intermediate U

To a solution of intermediate T in methylene chloride (10 mL) was slowly added tin(II)tris-benzenethiolate triethylamine complex (12 mL of a 0.5M solution in methylene chloride). After 10 minutes, an additional equivalent of tin reagent was added. After an additional 15 minutes, an additional equivalent was added. After 15 minutes, ethyl acetate (250 mL) was added and the mixture extracted with 1N aqueous sodium hydroxide solution (250 mL). The mixture was dried (sodium sulfate) and concentrated under reduced pressure. Toluene was added and the solvent removed under reduced pressure to give an oil which was used in the next transformation without further purification.

Example 21

Intermediate V

To a cooled (0° C.) solution of intermediate U (2 mmol) in methylene chloride (5 mL) was added 3-ketotetradecanoic acid (997 mg), prepared by the method of Christ, et al., European patent application 92309057.5, followed by 1-(3-dimethylaminopropyl)-3-ethylcarbodiimide hydrochloride (1.5 g) and the mixture stirred for approximately 30 minutes. The mixture was diluted with methylene chloride (150 mL), washed with 1N aqueous sodium hydroxide, dried (sodium sulfate) and the solvent removed under reduced pressure. Chromatography on silica followed by chromatography on basic alumina gave 1.64 g of intermediate V.

Example 22

Intermediate W

A solution of intermediate V (1.45 g) in glacial acetic acid (5 mL) was added to a suspension of well stirred zinc copper couple (14 g) in acetic acid (10 mL). The mixture was stirred for 15 minutes and additional zinc/copper couple (10 g) was added. After an additional 15 minutes, the mixture was filtered through diatomaceous earth which was then washed with ethyl acetate. The combined washings were diluted with toluene and the solvent removed under reduced pressure. The residue was chromatographed on a bilayered mixture of basic alumina and silica to give intermediate W which was used without further purification.

Example 23

Intermediate X

A solution of intermediate W (1.02 mmol) and cis-vaccenic acid (575 mg) was dissolved in toluene (5 mL) three times and the solvent removed under reduced pressure. The dried residue was dissolved in methylene chloride (3 mL) and 1-(3-dimethylaminopropyl)-3-ethylcarbodiimide hydrochloride (780 mg) was added and the mixture stirred for 3 hours. The mixture was diluted with methylene chloride and chromatographed directly to give 734 mg of intermediate X. Further chromatography of the impure fractions gave an additional 58 mg of material.

Example 24

Intermediate Y

To a solution of intermediate X (785 mg) in methylene chloride (10 mL) was added a solution of 48% aqueous hydrogen fluoride in acetonitrile (15 mL). The mixture was stirred for 90 minutes, diluted with methylene chloride (50 mL), washed with water, and with aqueous sodium bicarbonate solution. The mixture was dried (sodium sulfate) and chromatographed to give intermediate Y, 719 mg.

Example 25

Intermediate Z

Intermediate Y (719 mg) was dissolved in methylene chloride and sodium sulfate (1.4 g) was added. Diallyidiisopropylphosphoramidite (189 $\mu$L) and tetrazole (162 mg) were added, the mixture stirred for 10 minutes and then cooled to –78° C. A solution of m-chloroperoxybenzoic acid (192 mg) in methylene chloride (4 mL) was added dropwise. The mixture was washed with aqueous sodium thiosulfate and with aqueous sodium bicarbonate, dried (sodium sulfate) and the solvent removed under reduced pressure. The residue was chromatographed to give 660 mg of intermediate Z.

Example 26

Compound 1

To a solution of tetrakis(triphenylphosphine)palladium (0) (166 mg) in 2 mL of tetrahydrofuran: acetic acid (10:1) mixture was added a solution of intermediate Z (660 mg) in 3 mL of the same solvent mixture. After 30 minutes, additional tetrakis(triphenylphosphine)palladium (0) was added. After an additional 1½ hours, toluene was added and the solvent removed under reduced pressure. The mixture was purified by chromatography on diethylaminoethylcellulose. The purified mixture was dissolved in 0.1N aqueous sodium hydroxide, filtered through a 0.45 $\mu$ sterile filter and purified by HPLC on a YMC-Pack ODS-AP column to give 130 mg of compound 1.

Analytical data for some of the compounds and intermediates made by the methods described above is given below:
Compound 1: $^1$H NMR (CD$_3$OD) δ: 5.3 (1H, m), 4.6 (1, m), 4.0 (m, m), 3.9 (1H, d), 3.7 (1H, t), 3.6 (1H, t), 3.4 (3H, s), 3.3 (3H, t), 2.6 (2H, t), 2.3 (2H, m), 2.0 (2H, m), 1.7–1.2 (m, m), 0.9 (6H, t).
$^{31}$P NMR (CD$_3$OD) δ:4.71, 3.98.
Compound 1: (M+Na)$^+$=1333
Compound 2: (M+3 Na)$^+$=1363
Compound 3: (M+3 Na)$^+$=1365
Compound 5: (M+Na)$^+$=1303

Compound 6: $(M+Na)^+=1359$
Compound 7: $(M+Na)^+=1305$
Compound 8: $(M+3\ Na)^+=1393$
Compound 10: $(M+Na)^+=1425$ Intermediate G: $^1$H NMR (CDCl$_3$) δ: d, (1H), 3.9–3.7 (m, multiple), 3.65 (t, 1H), 3.37 (s,3H), 3.2 (m,2H), 1.75 (q, 2H), 1.52 (s,3H), 1.4 (s,3H), 1.3 (broad m,multiple), 0.95 (s,9H), 0.9 (t,3H), and 0.2 (d,6H)

Intermediate H: $^1$H NMR (CDCl$_3$) δ:4.58 (d,1H), 4.09 (m,2H), 3.9 (dd,1H), 3.75 (dd,1H), 3.7 (m,1H), 3.5 (t,1H), 3.37 (s,3H), 3.23 (t,1H), 3.05 (t,1H), 1.8 (m,2H), 1.68 (m,1H), 1.5 (m,1H), 1.3 (broad m,multiple), 0.95 (s,9H), 0.9 (t,3H), 0.2 (d,6H).

Intermediate I: $^1$H NMR (CDCl$_3$) δ:4,52 (d,1H), 4.05 (m,2H), 3.75 (m,1H), 3.67 (t,1H), 3.5 (t,1H), 3.45 (s,3H), 3.35 (s,3H), 3.25 (t,1H), 3.05 (t,1H), 1.8 (m,2H), 1.65 (m,1H), 1.5 (m,1H), 1.3 (broad s,m), 0.95 (s,9H), 0.9 (t,3H), 0.2 (s,6H)

IntermediateJ: $^1$H NMR (CDCl$_3$) δ:5.95 (m,2H), 5.35 (d,1H), 5.22 (d,1H), 4.6 (q,2H), 4.5 (d,1H), 4.32 (q,1H), 3.9–3.75 (m,3H), 3.7 (dd,1H), 3.65 (dd,1H), 3.45 (m,1H), 3.38 (s,3H), 3.33 (s,3H), 3.27 (t,1H), 3.2 (t,1H), 1.9–1.75 (m,3H), 1.5 (m,1H), 1.3 (broad m,multiple), 0.95 (s,9H), 0.9 (t,3H), 0.2 (s,6H)

Intermediate L: $^1$H NMR (CDCl$_3$) δ:5.95 (d,1H), 5.4 (d,2H), 5.25 Z(d,2H), 4.95 (d,1H), 4.7 (q,2H), 4.55 (q,2H), 4.32 (q,1H), 3.9–3.75 (m,3H), 3.7 (dd,1H), 3.65 (dd,1H), 3.55 (m,1 H), 3.4 (m,1H), 3.4 (s,3H), 3.3 (s,3H), 3.25 (m,1H), 1.75 (m,multiple), 1.5–1.4 (m,2H), 1.3 (broad s,multiple), 0.95–0.9 (broad s,12H), 0.2 (d,6H)

Intermediate M: $^1$H NMR (CDCl$_3$) δ:5.95 (m,2H), 5.75 (d,1 H), 5.4 (d,1 H), 5.25 (d,2H), 4.75–4.65 (dd,2H), 4.6 (q,1 H), 4.3 (q,1 H), 4.1 (m,2H), 3.9 (m,2H), 3.65 (m,1 H), 3.4 (s,3H), 3.25 (s,3H), 1.75 (broad m,2H), 1.55–1.4 (m,2H), 1.3 (broad s,multiple), 0.9 (t,3H)

Intermediate O; $^1$H NMR (CDCl$_3$) δ: 4.5 (d,1 H), 3.8 (dd,1 H), 3.78 (m,2H), 3.6 (m,multiple), 3.2 (m,2H), 1.5 (s,3H), 1.4 (s,3H), 1.3 (broad s, multiple), 0.95 (s,9H), 0.9 (t,3H), 0.18 (d,6H)

Intermediate P: $^1$H NMR (CDCl$_3$) δ:4.5 (d,1H), 3.75 (dd, 2H), 3.6 (q,2H), 3.5 (t,1H), 3.3 (m,1H), 3.2 (t,1H), 3.0 (t,1H), 1.6 (m,2H), 1.25 (broad s,multiple), 0.95 (s,9H), 0.9 (t,3H), 0.18 (d,6H)

Intermediate Q: $^1$H NMR (CDCl$_3$) δ:4.5 (d,1H), 3.82 (t,2H), 3.7 (m,2H), 3.6 (t,1H), 3.3 (m,1H), 3.2 (t,1H), 3.05 (q,2H), 1.6 (m,2H), 1.3 (broad s,multiple), 0.95 (s,9H), 0.88 (s,9H), 0.85 (t,3H), 0.2 (d,6H), 0.1 (d,6H)

Intermediate R: $^1$H NMR (CDCl$_3$) δ: 5.9 (m,1H), 5,4–5.25 (dd,2H), 4.75 (t,1H), 4.6 (d,2H), 4.45 (d,1H), 3.75 (q,1H), 3.7 (d,2H), 3.53 (q,1H), 3.38 (m,1H), 3.25 (t,1H), 3.15 (t,1H), 1.5 (t,2H), 1.25 (s, multiple), 0.95(s,9H), 0.85 (m,12H), 0.2 (s,6H), 0.07 (s,6H)

Intermediate S: $^1$H NMR (CDCl$_3$) δ: 5.9 (m,1H), 5.4–5.25 (dd,2H), 4.75 (t,1H), 4.6 (d,2H), 4.52 (d,1H), 3.7 (m,multiple), 3.65–3.6 (dd,2H), 3.55 (q,1H), 3.4 (m,1H), 3.28 (t,1H), 3.2 (t,1H), 1.5 (t,2H), 1.3 (s, multiple), 0.9 (s,9H), 0.85 (t,3H), 0.2 (s,6H)

Intermediate T: $^1$H NMR (CDCl$_3$) δ: 5.9 (m,3H), 5.6 (d,1H), 5.4–5.2 (m,6H), 4.8 (d,1H), 4.7–4.6 (m,2H), 4.55 (q,1H), 4.5 (d,1H), 4.3 q,1H), 3.8–3.7 (m,multiple), 3.6 (dd, 1H), 3.5 (m,multiple), 3.35 (s,3H), 3.2 (s,3H), 3.15 (t,1H), 1.7 (m,2H), 1.5 (m,2H), 1.3 (s,multiple), 0.95 (t,6H), 0.2 (t,6H)

Intermediate V: $^1$H NMR (CDCl$_3$) δ: 7.3 (d,1H), 5.95 (m,3H), 5.6 (d,1H), 5.4–5.2 (m,6H), 4.95 (d,1H), 4.8 (d,1H), 4.7–4.5 (m,multiple)4.3 (q,1H), 3.9–3.65 (m,multiple), 3.6 (m,multiple), 3.45 (t,1H), 3.4 (t,3H), 3.35 (s,2H), 3.28 (3H), 2.5 (t,2H), 1.8 (m,2H), 1.6 (m,2H), 1.45 (m,2H), 1.3 (broad s,multiple), 0.95–0.8 (m,18H), 0.15 (d,6H)

Intermediate X: $^1$H NMR (CDCl$_3$) δ: 7.3 (d,1H), 5.95 (m,4H), 5.4–5.2 (m,8H), 4.95 (d,1H), 4.8 (d,1H), 4.7 (t,1H), 4.6 (d,1H), 4.55 (q,1H), 4.3 (q,1H), 4.1 (t,1H), 3.9 (q,1H), 3.8 (t,1H), 3.7–3.5 (m,multiple), 3.45 (t,1H), 3.35 (s,3H), 3.3 (s,2H), 3.28 (s,3H), 2.5 (t,2H), 2.2 (t,1H), 2 (d,1H), 1.7 (q,2H), 1.6 (m,2H), 1.3 (s,multiple), 0.950.8 (m,21), 0.15 (d,6H)

Intermediate Y: $^1$H NMR (CDCl$_3$) δ: 6.65 (d,1H), 6.55 (d,1H), 5.905 (m,5H), 5.7 (m,1H), 5.4–5.2 (m,12H). 4.8 (m,2H), 4.6 (d,1H), 4.5 (m,10H), 4.3 (q,1H), 4.1 (m,1H), 3.85–3.45 (m,multiple), 3.4 (s,3H), 3.35 (s,3H), 3.25 (s,3H), 3.2 (t,1H), 2.5 (dd,2H), 2.2 (t,2H), 2 (m,mutiple), 1.7–1.2 (m,mutiple), 0.9 (t,12H).

BIOLOGICAL EXAMPLES

Both bacterial LPS and bacterial lipid A elicit production of tumor necrosis factor (TNF), IL-1β, IL-6 and IL-8 as well as other cytokines and cellular mediators in human whole blood and in a human macrophage cell lines. Generation of pathophysiological quantities of these cytokines has been found to play an important part in the initiation of the systemic inflammatory response syndrome and septic shock. The liposaccharide analogs described herein inhibit such LPS-and/or lipid A-mediated induction of cytokines as demonstrated by the following experiments.

Example A

In Vitro Inhibition of LPS-Induced Production of Cytokines

Whole human blood was prepared and tested as described (Rose et al. (1995) Infection and Immunity, 63 833–839). HL-60 cells were cultured in RPMI medium supplemented with 10% fetal calf serum and antibiotics, and induced to differentiate into macrophages by treatment with 0.1 μM 1,25-dihydroxycholecalciferol (Vitamin D3; Biomol Research Laboratories, Plymouth Meeting, Pa.), and tested for LPS mediated generation of IL-8. Briefly, bacterial LPS (i.e., from E. coli 0111:B4; Sigma Chemicals, St. Louis, Mo.) at 10 ng/mL or lipid A (Daiichi Chemicals, Tokyo, Japan) were added as 10-fold concentrated solutions in $Ca^{++}$, $Mg^{++}$free Hank's balanced salt solution (CMF-HBSS; Gibco). In experiments involving analogs of the present invention, the analog was added immediately before addition of LPS or lipid A in CMF-HBSS (e.g., between 0 and 100 μM as a 10× concentrated aliquot). Following incubation of three hours, plasma was prepared from whole blood, or culture supernatant was removed and assayed for the presence of the indicated cytokine using an ELISA assay kit from Genzyme (Cambridge, Mass.) following the instructions of the manufacturer, however, any other standard ELISA kits may be utilized. Experiments were performed in triplicate at least twice.

The lipid A analogs inhibited LPS-induced production of TNF in human whole blood in a concentration-dependent manner. Of the analogs tested, Compound 1 was found to be one of the most effective compounds. The results of this test are as shown in FIG. 1. Compound 1 inhibits LPS-induced production of TNF, exhibiting an IC$_{50}$ of approximately 1.5 nM. Other analogs found to inhibit LPS-induced TNF production included compound 2, compound 3, compound 4, compound 5, compound 6, compound 7, compound 8, compound 9, and compound 10. These compounds exhibited IC$_{50}$s of between 1.5 nM and 159 nM.

Compound 1 also inhibited LPS-mediated induction of IL-8 in HL-60 (human macrophage-like) cells. Inhibition of IL-8 generation was complete at concentrations of 1 nM and greater Compound 1 when either LPS or lipid A was used as agonist.

Compounds of this invention similarly inhibited the LPS-induced production of other cytokines in human whole blood, even though some of these cytokines were generated several hours after addition of LPS. For instance, IL-1β, and IL-6 requires four or more hours for maximum levels to be reached, while IL-8 reaches maximum levels ten or more hours after LPS addition. Using methods described above, compounds of this invention were added at a concentrations between 0 and 10 μM and LPS was added at 10 ng/mL. Inhibition of production of TNF, IL-1β, IL-6, and IL-8 was measured as a function of time after addition of LPS. This inhibition of cytokine generation was also found to be concentration dependent, but in all cases, suppression of all cytokine synthesis was >90% at compound 1 concentrations of 10 nM and more for up to 24 hours after addition of LPS.

Example B
Persistence of compounds in human whole blood

Figure 2:
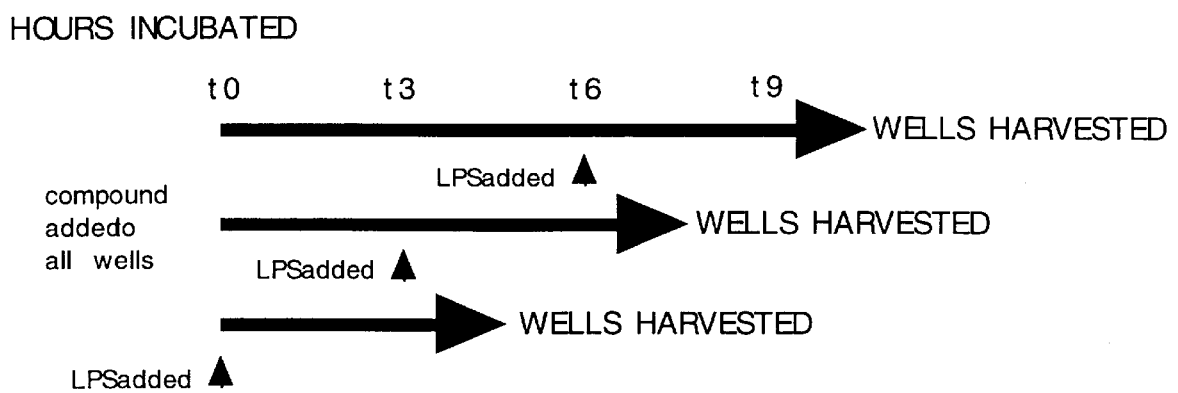
FIG. 2 depicts the general scheme used to analyze antagonistic efficacy of drug after incubation in whole blood for various times.

Although some of the compounds of this invention are not rapidly removed from the circulation, their activity diminishes with a half life of 1–3 hours. In order to maintain antagonistic efficacy, this rapid deactivation may require continuous administration. The study of this deactivation has led to the development of an assay to measure in vitro deactivation of drugs in human whole blood. This is done by preincubating lipid A antagonists with blood for various periods of time followed by addition of the LPS "challenge" as described above, incubation for three hours, and assay for released cytokines. A schematic for this assay is shown in FIG. 2.

Figure 3:
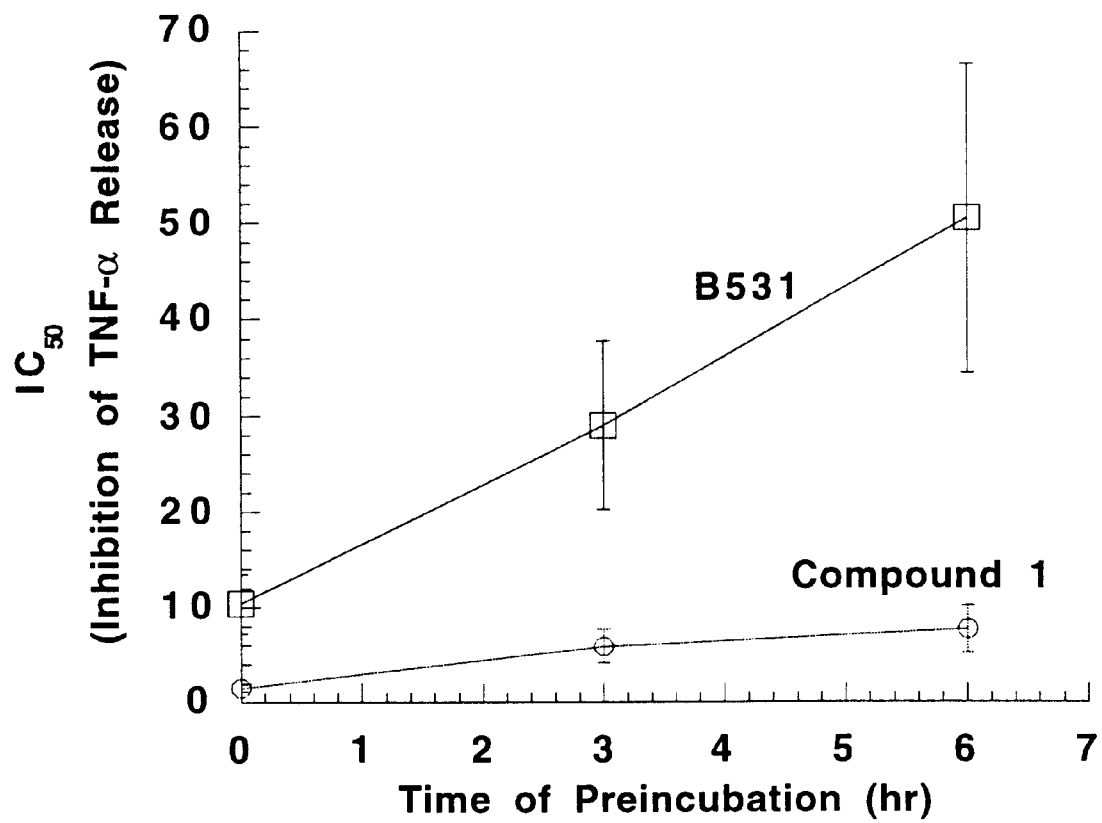
FIG. 3 depicts the relationship between time versus ability of the test compound to inhibit TNF-α and demonstrates that Compound 1 has a superior duration of action as an LPS antagonist than does B531. These data are the average of 7 separate experiments each run in triplicate.

Using this assay, it can be demonstrated that B531, as described by Christ, et al., U.S. application Ser. No. 07/935,050, "deactivates" (loses activity with increasing time of preincubation). As shown in FIG. 3, compound 1 also deactivates, but its superior activity and decreased deactivation rate makes it as active after 6 hours as B531 was just after its addition. These data are the average of 7 separate experiments run in triplicate.

Example C
Inhibition of TNF or IL-6 Production in in vitro animal model systems

LPS-induced TNF or IL-6 production was inhibited by compounds of the present invention in whole blood or macrophages isolated from guinea pigs, rats and mice. Hartley-White guinea pig (Elm Hill Breeders, Chelmsford, Mass.) and C57BU6 mouse (Jackson Labs, Bar Harbor, Me.) macrophages were isolated from the abdomen of primed animals. Priming was accomplished by intraperitoneal injection of 2 mg of Bacillus calmette guerin(BCG; RIBI Immunochemical Research, Inc., Hamilton, Mont.) at a concentration of 10 mg/mL in physiological saline for mice and 2 mg of BCG at a concentration of 2 mg/7 mL in mineral oil for guinea pigs. Three days post-injection, peritoneal macrophages were isolated from the abdomen of the animals by standard techniques. Cells were allowed to adhere to culture plates for two to three hours and were then cultured with RPMI 1640 medium containing 10% fetal calf serum and LPS (final concentration of 10 ng/mL) was added as described above. To test inhibition, compounds of this invention (at a concentration of between 0 and 100 μM) were added to the culture medium just prior to LPS addition. Following a three-hour incubation period, guinea pig, mouse and rat TNF levels and/or IL-6 levels were assayed by ELISA, or by the cytolytic bioassay described in *Lymphokines* 2:235, 1981 for TNF released from guinea pig macrophages. In mouse peritoneal macrophages, Compound 1 provided effective inhibition ($IC_{50}$=16 nM for IL-6 and 20 nM for TNF, respectively); in guinea pig macrophages, the $IC_{50}$ for TNF release was 0.3 nM and in rat peritoneal macrophages, the $IC_{50}$ for release of TNF was 11 nM.

Example D
In Vivo Assays

BCG-primed mice (Vogel, S. et al. J. Immunology 1980, 124, 2004–2009) were utilized as an in vivo assay system for monitoring the inhibitory effects of lipid A analogs on (1) LPS-induced TNF production and (2) LPS-induced lethality as follows.

Five week old male C57BL/6 mice (supra) were primed by intravenous tail vein injection with 2 mg of BCG. Ten days post-injection, *E. coli* LPS (supra) in pyrogen-free 5% glucose solution (Otsuka Pharmaceuticals Inc., Tokyo, Japan) was administered intravenously through the tail vein of the BCG-primed mice. LPS was administered at 1–3 μg/mouse for both TNF production and mortality studies. The test compound was administered as a component of the injected LPS solution at a concentration of between 3 and 300 μg/mouse. Plasma was obtained one hour post LPS injection, and TNF was assayed by the ELISA assay described above. Mortality resulting from septic shock was recorded for 36 hours after LPS injection.

Compounds of this invention effectively suppressed the production of TNF following administration of LPS. Compound 10 and Compound 1 effectively inhibited TNF production in vivo in mice ($ED_{50s}$=5 and 10.6 μg/mouse, respectively). Compound 2, compound 3, compound 4, compound 5, compound 6, compound 7, compound 8, and compound 9 also inhibited TNF production with $ED_{50}$s between 10 and 200 μg/mouse with compounds 5, 6, and 7 giving $ED_{50}$ values >100.

In parallel experiments carried out in guinea pigs, these analogs were also effective inhibitors of LPS-induced TNF production in vivo (optimum $ED_{50}$'s between 2.3 and 6.1 μg/guinea pig for compound 1, compound 7, and compound 10.

Therapy

The lipid A analogs described herein provide useful therapeutics for the treatment or prevention of any LPS-mediated inflammation or disorder. Such disorders include without limitation: endotoxemia (or sepsis syndrome) resulting from a gram negative bacteremia (with its accompanying symptoms of fever, generalized inflammation, disseminated intravascular coagulation, hypotension, acute renal failure, acute respiratory distress syndrome, hepatocellular destruction, and/or cardiac failure); and LPS-mediated exacerbation of latent or active viral infections (e.g., infection with HIV-1, cytomegaloviruses, herpes simplex, and influenza virus).

The lipid A analog is typically administered in a pharmaceutically acceptable formulation, e.g., dissolved in physiological saline (which may include 5% glucose). When the lipid A analog is provided for the treatment of a viral infection, it may be administered in conjunction with appropriate viricidal agents. The Lipid A analog may be stored as a freeze-dried formulation.

Lipid A analogs are administered in dosages which provide suitable inhibition of LPS activation of target cells; generally, these dosages are, preferably, between 0.01–50 mg/patient/day, more preferably, between 0.05–25 mg/patient/day, and most preferably, between 1 and 12 mg/patient/day.

The drug should be injected or infused as soon as possible when SIRS can be diagnosed using clinical predictors such as the APACHE score (Knaus, et al., 1991 Chest 100: 1619–36 and Knaus, et al., 1993 JAMA: 1233–41) or other clinical predictors. In addition, injection or infusion should commence as soon as possible after exposure to endotoxin or diagnosis of systemic gram negative bacterial infection, especially if a more rapid or early diagnostic indicator of systematic gram negative infection becomes available.

Prophylactic indications for use of these drugs may include their use when exposure to endotoxin can be anticipated. This can occur when:

1) there is an increased probability of elevation of systemic (blood-borne) endotoxin from systemic or localized gram negative bacterial infection (such as during surgery);

2) there is an increased probability that blood levels of endotoxin may increase. In the normal physiological state, endotoxin only minimally translocates across the gut endothelium into splanchnic circulation. This translocated endotoxin is usually then cleared by the liver (and possibly other cells and organs). Increases in blood endotoxin levels can occur when the rate of endotoxin clearance by the liver (or other endotoxin sequestering cells or organs) decreases. Augmentation of gut translocation can occur after gut ischemia, hypoxia, trauma, or other injury to the integrity of the gut lining (or by drug or alcohol toxicity). Blood levels of endotoxin increase when liver function is compromised by disease (cirrhosis), damage (surgery or trauma), or temporary removal (as during liver transplantation);

3) there is an acute or chronic exposure to externally-derived endotoxin resulting in inflammatory response; this exposure can be caused by inhalation or other means of uptake of endotoxin. One example of SIRS-inducing endotoxin uptake is corn dust fever (Schwartz, et al., 1994 Am J Physiol. 267: L609–17), which affects workers in the grain industry, for example, in the American mid-west. Such workers can be prophylactically treated, e.g., daily, by inhaling an aerosolized formulation of the drug prior to beginning work in, e.g., fields or grain elevators.

For most other prophylactic and therapeutic applications, IV infusion or bolus injection will be used. Injection is most preferable, but infusion may be warranted in some cases by pharmacokinetic requirements.

The treatment should be initiated as soon as possible after diagnosis of SIRS, and should continue for at least three days, or when assessment of risk of mortality is reduced an acceptable level.

What is claimed is:

1. A compound of the formula:

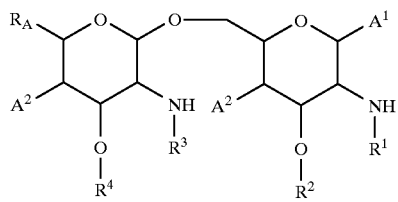

where $R^1$ is selected from the group consisting of

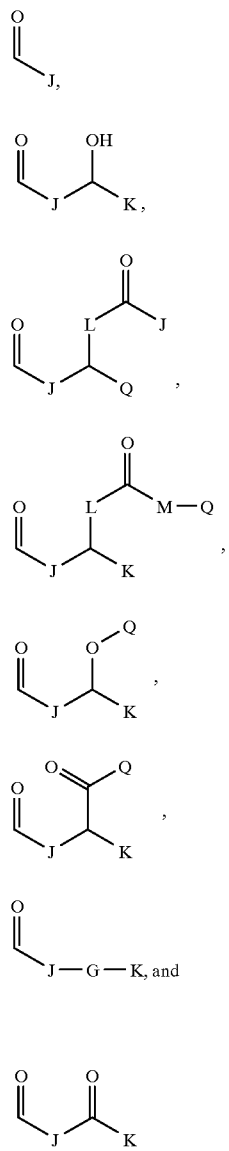

where each J, K and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 alyl,

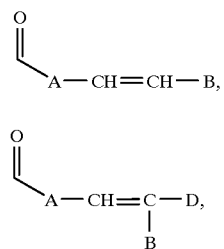

-continued

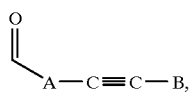

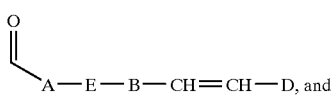

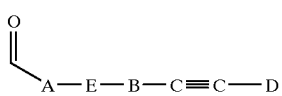

where E is NH, O, S, SO, or $SO_2$; each A, B and D, independently, is straight or branched C1 to C15 alkyl;

$R^4$ is selected from the group consisting of straight or branched C4 to C20 alkyl, and

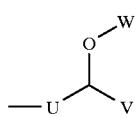

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J', J'—OH, —J'—O—K',—J'—O—K'—OH, and —J'—O—$PO(OH)_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of

OH,

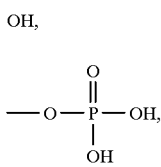

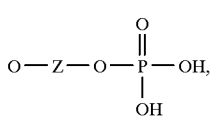

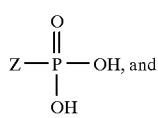

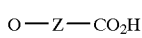

where Z is straight or branched C1 to C10 alkyl;
or a pharmaceutically acceptable salt thereof.

2. compound of claim 1 with the formula:

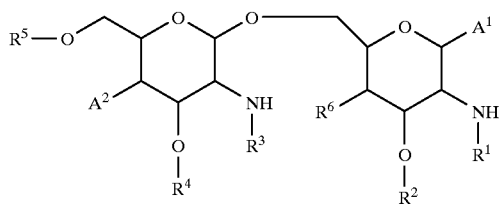

where $R^1$ is selected from the group consisting of

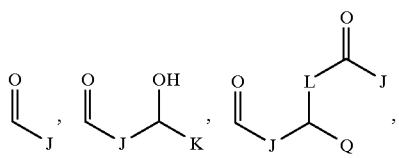

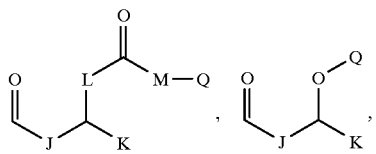

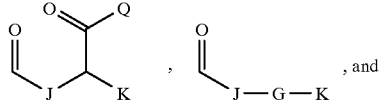

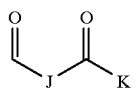

where each J, K and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 alyl,

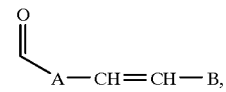 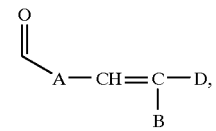

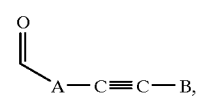

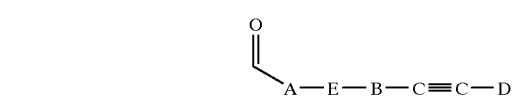

where E is NH, O, S, SO, or $SO_2$; each A, B and D, independently, is straight or branched C1 to C15 alkyl;

$R^4$ is selected from the group consisting of straight or branched C4 to C20 alkyl, and

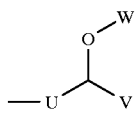

where each U and V, independently, is straight or branched C2 to C15 alkyl and W is hydrogen or straight or branched C1 to C5 alkyl;
$R^5$ is selected from the group consisting of hydrogen, J', —J'—OH, —J'—O—K', —J'—O—K'—OH and —J'—O—PO(OH)$_2$, where each J' and K', independently, is straight or branched C1 to C5 alkyl;
$R^6$ is selected from the group consisting of hydroxy, halogen, C1 to C5 alkoxy and C1 to C5 acyloxy;
$A^1$ and $A^2$, independently, are selected from the group consisting of

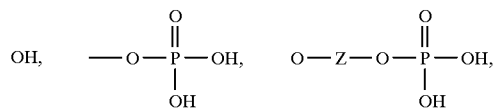

where Z is straight or C1 to C10 alkyl;
or a pharmaceutically acceptable salt thereof.

3. A compound of claim 2 where $R^2$ is C8 to C15 straight or branched alkyl.

4. A compound of claim 2 where $R^2$ is C9 to C12 straight or branched alkyl.

5. A compound of claim 2 where $R^2$ is C10 straight or branched alkyl.

6. A compound of claim 2 where $A^1$ and $A^2$, independently, are OH or —O—PO(OH)$_2$.

7. A compound of claim 2 where $R^6$ is hydroxy.

8. A compound of claim 2 where $R^5$ is C1 to C5 straight or branched alkyl.

9. A compound of claim 2 where $R^1$ is selected from the group consisting of

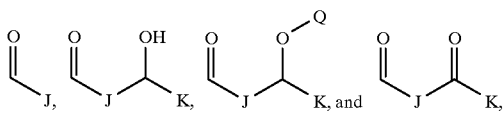

where each J, K and Q, independently, is straight or branched C1 to C15 alkyl.

10. A compound of claim 2 where $R^4$ is selected from the group consisting of straight or branched C4 to C20 alkyl, and

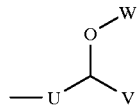

where U is straight or branched C2 to C5 alkyl, V is straight or branched C5 to C12 alkyl, and W is hydrogen or straight or branched C1 to C5 alkyl.

11. A compound of claim 2 having the following structure

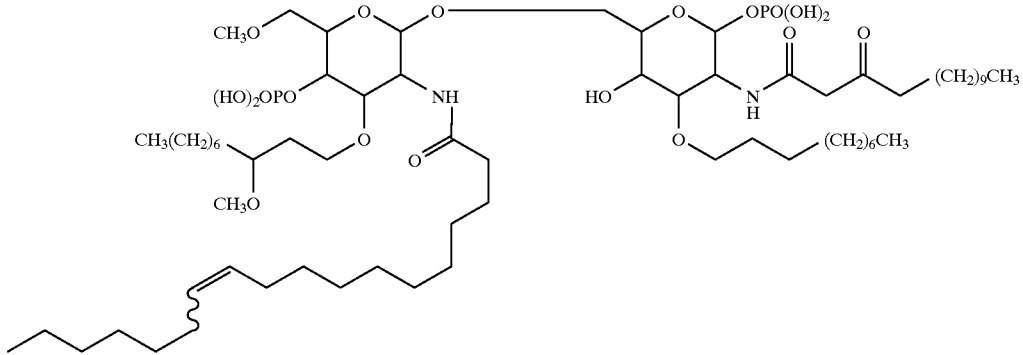

or a pharmaceutically acceptable salt thereof.

12. A compound of claim 2 having the following structure

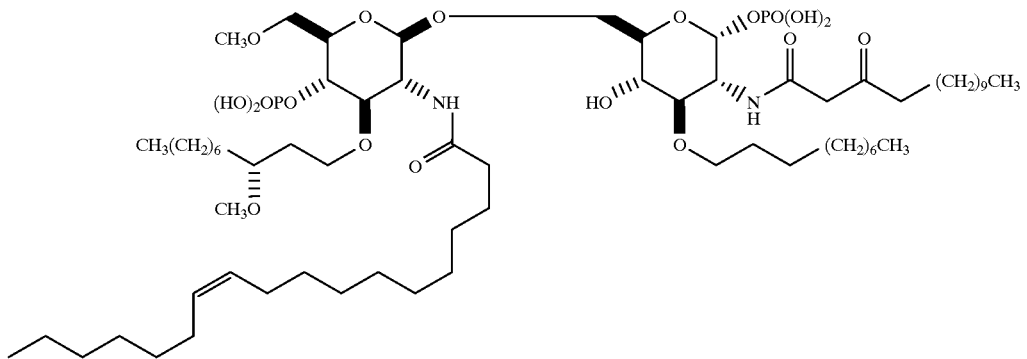
or a pharmaceutically acceptable salt thereof.
13. A method for treating sepsis in a patient, said method comprising administering compound of claim 1 to said patient by bolus injection.

UNITED STATES PATENT AND TRADEMARK OFFICE
CERTIFICATE OF CORRECTION

PATENT NO.   : 5,935,938
DATED        : August 10, 1999
INVENTOR(S)  : William J. Christ, Daniel P. Rossignol, Seiichi Kobayashi and Tsutomu Kawata It is certified that error appears in the above-identified patent and that said Letters Patent is hereby corrected as shown below:

Columns 3 and 4,
At the top of columns 3 and 4, replace:

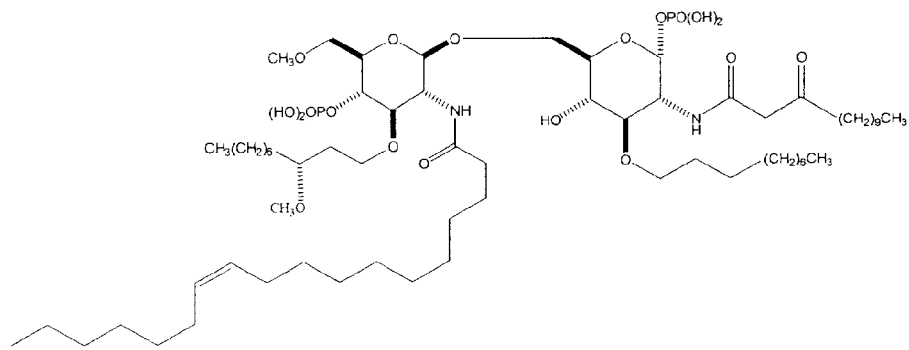

Compound 1 with:

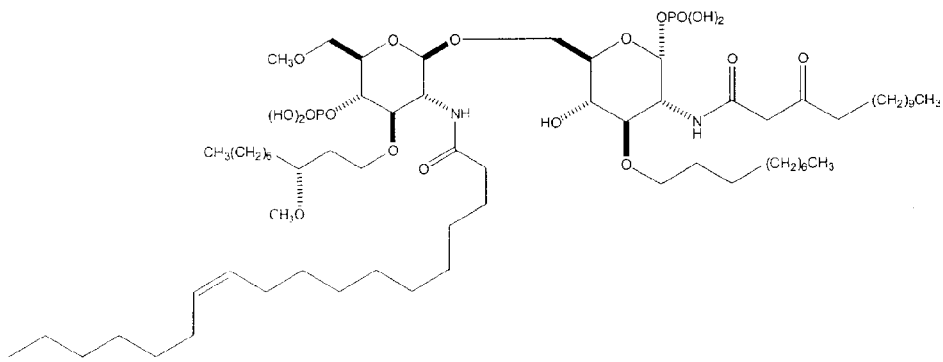

Compound 1

Column 65,
Lines 58-65, on the right side of the molecule, replace "$A^2$" with -- $R^6$ --;

Column 66,
Line 55, replace "alyl" with -- acyl --;

UNITED STATES PATENT AND TRADEMARK OFFICE
CERTIFICATE OF CORRECTION

PATENT NO. : 5,935,938
DATED : August 10, 1999
INVENTOR(S) : William J. Christ, Daniel P. Rossignol, Seiichi Kobayashi and Tsutomu Kawata It is certified that error appears in the above-identified patent and that said Letters Patent is hereby corrected as shown below:

Column 67,
Line 34, replace "J' -OH" with --  -J' -OH --;

Column 68,
Line 1, before "compound", add -- A --;
Line 43, replace "alyl" with -- acyl --;

Column 69,
Line 31, after "straight or", add -- branched --;

Column 72,
Line 18, after "administering", add -- the --.

Signed and Sealed this

Thirteenth Day of August, 2002

Attest:

JAMES E. ROGAN
Attesting Officer   Director of the United States Patent and Trademark Office